US009116156B2

(12) United States Patent
Andres et al.

(10) Patent No.: US 9,116,156 B2
(45) Date of Patent: Aug. 25, 2015

(54) ASC AS A MARKER FOR CHRONIC OBSTRUCTIVE PULMONARY DISEASE (COPD)

(71) Applicant: Roche Diagnostics Operations, Inc., Indianapolis, IN (US)

(72) Inventors: Herbert Andres, Penzberg (DE); Johann Karl, Peissenberg (DE); Julia Riedlinger, Ottobrunn (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 14/022,273

(22) Filed: Sep. 10, 2013

(65) Prior Publication Data
US 2014/0004543 A1 Jan. 2, 2014

Related U.S. Application Data

(63) Continuation of application No. PCT/EP2012/053847, filed on Mar. 7, 2012.

(30) Foreign Application Priority Data

Mar. 11, 2011 (EP) .................................... 11157917

(51) Int. Cl.
G01N 33/68 (2006.01)
(52) U.S. Cl.
CPC ........ G01N 33/6893 (2013.01); G01N 33/6884 (2013.01); G01N 2333/4703 (2013.01); G01N 2800/122 (2013.01)
(58) Field of Classification Search
None
See application file for complete search history.

(56) References Cited

U.S. PATENT DOCUMENTS

| 5,807,522 | A | 9/1998 | Brown et al. | |
| 7,731,938 | B2* | 6/2010 | Karl et al. | 424/9.1 |
| 2009/0075312 | A1* | 3/2009 | Wild et al. | 435/15 |
| 2010/0273191 | A1* | 10/2010 | Arber | 435/7.23 |

FOREIGN PATENT DOCUMENTS

| EP | 0404097 A2 | 12/1990 |
| WO | 93/01161 A1 | 1/1993 |
| WO | 2004/059293 A2 | 7/2004 |
| WO | 2006/066915 A1 | 6/2006 |
| WO | 2006/105252 A3 | 10/2006 |
| WO | 2009/074275 A1 | 6/2009 |
| WO | 2010/004092 A1 | 1/2010 |

OTHER PUBLICATIONS

Kim et al. (Am. J. Resp. Crit Med 2010 vol. 181, p. 797-805).*
International Search Report issued May 15, 2012 in Application No. PCT/EP2012/053847, 5 pages.
Aksoy, Saime et al., "Human Liver Nicotinamide N-Methyltransferase cDNA Cloning, Expression, and Biochemical Characterization," The Journal of Biological Chemistry, May 20, 1994, pp. 14835-14840, vol. 269, No. 20.
Apostolou, Andria et al., "Armet, a UPR-upregulated protein, inhibits cell proliferation and ER stress-induced cell death," Experimental Cell Research, 2008, pp. 2454-2467, vol. 314.
Barzilay, Gil et al., "Identification of critical active-site residues in the multifunctional human DNA repair enzyme HAP1," Nature Structural Biology, Jul. 1995, pp. 561-567, vol. 2, No. 7.
Barzilay, Gil and Hickson, Ian D., "Structure and function of apurinic/apyrimidinic endonucleases," BioEssays, 1995, pp. 713-719, vol. 17, No. 8.
Beernink, Peter T. et al., "Two Divalent Metal Ions in the Active Site of a New Crystal Form of Human Apurinic/Apyrimidinic Endonuclease, Ape1: Implications for the Catalytic Mechanism," Journal of Molecular Biology, 2001, pp. 1023-1034, vol. 307.
Breiman, Leo, "Random Forests," Machine Learning, 2001, pp. 5-32, vol. 45.
Burmeister, G. and Gallacchi, G., "A Selective Method for Determining MRP8 and MRP14 Homocomplexes and Heterocomplexes by Sandwich ELISA for the Discrimination of Active and Non-Active Osteoarthritis from Rheumatoid Arthritis in SERA and Synovial Fluids," Inflammopharmacology, 1995, pp. 221-230, vol. 3.
Donaldson, Gavin C., "C-reactive Protein Does It Predict Mortality?" American Journal of Respiratory and Critical Care Medicine, 2007, pp. 209-210, vol. 175.
Foell, D. et al., "Expression of the pro-inflammatory protein S100A12 (EN-RAGE) in rheumatoid and psoriatic arthritis," Rheumatology, 2003, pp. 1383-1389, vol. 42.
Friedman, Jerome H., "Regularized Discriminant Analysis," Journal of the American Statistical Association, Mar. 1989, pp. 165-175, vol. 84, No. 405.
Fujita, Miyoshi et al., "C-reactive protein levels in the serum of asthmatic patients," Annals of Allergy, Astha & Immunology, 2007, pp. 48-53, vol. 99.
Gearing, Andrew J. H. et al., "Soluble Forms of Vascular Adhesion Molecules, E-Selectin, ICAM-1, and VCAM-1: Pathological Significance," Annals of the New York Academy of Sciences, 1992, pp. 324-331, vol. 667.
Goldstein, Leslie A. et al., "Molecular cloning of seprase: a serine integral membrane protease from human melanoma," Biochimica et Biophysica Acta, 1997, pp. 11-19, vol. 1361.
Gorman, Michael A. et al., "The crystal structure of the human DNA repair endonuclease HAP1 suggests the recognition of extra-helical deoxyribose at DNA abasic sites," The EMBO Journal, 1997, pp. 6548-6558, vol. 16, No. 21.
Greenbaum, Dov et al., "Comparing protein abundance and mRNA expression levels on a genomic scale," Genome Biology, 2003, pp. 117.1-117.8.
Gygi, Steven P. et al., "Correlation between Protein and mRNA Abundance in Yeast," Molecular and Cellular Biology, Mar. 1999, pp. 1720-1730, vol. 19, No. 3.
Hasan, Sameez et al., "Regulation of Human Flap Endonuclease-1 Activity by Acetylation through the Transcriptional Coactivator p300," Molecular Cell, Jun. 2001, pp. 1221-1231, vol. 7.

(Continued)

Primary Examiner — Jacob Cheu
(74) Attorney, Agent, or Firm — Stinson Leonard Street LLP

(57) ABSTRACT

An in vitro method aiding in the assessment of chronic obstructive pulmonary disease (COPD). The disclosure further relates to a method for assessing COPD from a sample, derived from an individual, by measuring the protein ASC in said sample in vitro.

16 Claims, 8 Drawing Sheets

(56) References Cited

OTHER PUBLICATIONS

Henry, Leonard R. et al., "Clinical Implications of Fibroblast Activation Protein in Patients with Colon Cancer," Clinical Cancer Research, Mar. 15, 2007, pp. 1736-1741, vol. 13, No. 6.

Hey, Thomas et al., "Artificial, non-antibody binding proteins for pharmaceutical and industrial applications," Trends in Biotechnology, Oct. 2005, pp. 514-522, vol. 23, No. 10.

Hiraoka, Lea R. et al., "Sequence of Human FEN-1, a Structure-Specific Endonuclease, and Chromosomal Localization of the Gene (FEN1) in Mouse and Human," Genomics, 1995, pp. 220-225, vol. 25.

Huang, Max Tze-Han et al., "Critical Role of Apoptotic Speck Protein Containing a Caspase Recruitment Domain (ASC) and NLRP3 in Causing Necrosis and ASC Spec Formation Induced by *Porphromonas gingivalis* in Human Cells," The Journal of Immunology, 2009, pp. 2395-2404, vol. 182.

Hogg, James C. et al., "The Nature of Small-Airway Obstruction in Chronic Obstructive Pulmonary Disease," The New England Journal of Medicine, Jun. 24, 2004, pp. 2645-2653, vol. 350, No. 26.

Holliger, Philipp et al., "'Diabodies': Small bivalent and bispecific antibody fragments," Proceedings of the National Academy of Sciences USA, Jul. 1993, pp. 6444-6448, vol. 90.

Hudson, Peter J. and Souriau, Christelle, "Engineered antibodies," Nature Medicine, Jan. 2003, pp. 129-134, vol. 9, No. 1.

Kim, Ho Cheol et al., "Expression and Functional Significance of Nicotinamide N-methyl Transferase in Skeletal Muscles of Patients with Chronic Obstructive Pulmonary Disease," American Journal of Respiratory and Critical Care Medicine, 2010, pp. 797-805, vol. 181.

Lee, Kyung N. et al., "A novel plasma proteinase potentiates α2-antiplasmin inhibition of fibrin digestion," Blood, May 15, 2004, pp. 3783-3788, vol. 103, No. 10.

Lee, Kyung N. et al., "Antiplasmin-cleaving enzyme is a soluble form of fibroblast activation protein," Blood, Feb. 15, 2006, pp. 1397-1404, vol. 107, No. 4.

Liu, Yuan et al., "Flap Endonuclease 1: A Central Component of DNA Metabolism," Annual Review of Biochemistry, 2004, pp. 589-615, vol. 73.

Mathers, Colin D. and Loncar, Dejan, "Projections of Global Mortality and Burden of Disease from 2002 to 2030," PLoS Medicine, Nov. 2006, pp. 2011-2030, vol. 3, Issue 11, e442.

Mizobuchi, Naomi et al., "ARMET is a Soluble ER Protein Induced by the Unfolded Protein Response via ERSE-II Element," Cell Structure and Function, 2007, pp. 41-50, vol. 32.

Murray, J. M. et al., "Structural and Functional Conservation of the Human Homolog of the *Schizosaccharomyces pombe* rad2 gene, Which Is Required for Chromosome Segregation and Recovery from DNA Damage," Molecular and Cellular Biology, Jul. 1994, pp. 4878-4888, vol. 14, No. 7.

Nathell, Lennart et al., "COPD diagnosis related to different guidelines and spirometry techniques," Respiratory Research, 2007, vol. 8, No. 89, 7 pages.

Nie, Lei et al., "Integrative Analysis of Transcriptomic and Proteomic Data: Challenges, Solutions and Applications," Critical Reviews in Biotechnology, 2007, pp. 63-75, vol. 27.

Park, John E. et al., "Fibroblast Activation Protein, a Dual Specificity Serine Protease Expressed in Reactive Human Tumor Stromal Fibroblasts," The Journal of Biological Chemistry, Dec. 17, 1999, pp. 36505-36512, vol. 274, No. 51.

Petrilli, Virginie et al., "The inflammasome," Current Biology, Current Science, 2005, R581, vol. 15.

Petrova, Penka S. et al., "MANF A New Mesencephalic, Astrocyte-Derived Neurotrophic Factor with Selectivity for Dopaminergic Neurons," Journal of Molecular Neuroscience, 2003, pp. 173-188, vol. 20.

Piñeiro-Sánchez, Mayra L. et al., "Identification of the 170-kDa Melanoma Membrane-bound Gelatinase (Seprase) as a Serine Integral membrane Protease," The Journal of Biological Chemistry, Mar. 21, 1997, pp. 7595-7601, 13366, vol. 272, No. 12.

Qui, Junzhuan et al., "Arginine Residues 47 and 70 of Human Flap Endonuclease-1 Are Involved in DNA Substrate Interactions and Cleavage Site," The Journal of Biological Chemistry, Jul. 2002, pp. 24659-24666, vol. 277, No. 27.

Rabe, Klaus F. et al., "Global Strategy for the Diagnosis, Management, and Prevention of Chronic Obstructive Pulmonary Disease GOLD Executive Summary," American Journal of Respiratory and Critical Care Medicine, 2007, pp. 532-555, vol. 176.

Robins, Peter et al., "Structural and Functional Homology between mammalian DNase IV and the 5'-Nuclease Domain of *Escherichia coli* DNA Polymerase I," The Journal of Biological Chemistry, Nov. 18, 1994, pp. 28535-28538, vol. 269, No. 46.

Robinson, William H. et al., "Autoantigen microarrays for multiplex characterization of autoantibody responses," Nature Medicine, Mar. 2002, pp. 295-301, vol. 8, No. 3.

Robinson, William H. et al., "Proteomics Technologies for the Study of Autoimmune Disease," Arthritis & Rheumatism, Apr. 2002, pp. 885-893, vol. 46, No. 4.

Ruczinski, Ingo et al., "Logic Regression," Journal of Computational and Graphical Statistics, 2003, pp. 475-511, vol. 12, No. 3.

Rush, John et al., "Immunoaffinity profiling of tyrosine phosphorylation in cancer cells," Nature Biotechnology, Jan. 2005, pp. 94-101, vol. 23, No. 1.

Saetta, M. et al., "Airway eosinophilia and expression of interleukin-5 protein in asthma and in exacerbations of chronic bronchitis," Clinical and Experimental Allergy, 1995, pp. 766-774, vol. 26.

Saetta, Marina et al., "Airway Eosinophilia in Chronic Bronchitis during Exacerbations," American Journal of Respiratory and Critical Care Medicine, 1994, pp. 1646-1652, vol. 150.

Saetta, Marina et al., "CD8+ T-Lymphocytes in Peripheral Airways of Smokers with Chronic Obstructive Pulmonary Disease," American Journal of Respiratory and Critical Care Medicine, 1998, pp. 822-826, vol. 157.

Sakurai, Shigeru et al., "Structural basis for recruitment of human flap endonuclease 1 to PCNA," The EMBO Journal, 2005, pp. 683-693, vol. 24.

Scanlan, Matthew J. et al., "Molecular cloning of fibroblast activation protein α, a member of the serine protease family selectively expressed in stromal fibroblasts of epithelial cancers," Proceedings of the National Academy of Sciences, Jun. 1994, pp. 5657-5661, vol. 91.

Schwanhäusser, Björn et al., "Global quantification of mammalian gene expression control," Nature, May 2011, pp. 337-341, vol. 473; Mar. 2013, pp. 126-127, vol. 495.

Shen, Binghui et al., "Essential Amino Acids for Substrate Binding and Catalysis of Human Flap Endonuclease 1," The Journal of Biological Chemistry, Apr. 19, 1996, pp. 9173-9176, vol. 271, No. 16.

Shen, Binghui et al., "Multiple but dissectible functions of FEN-1 nucleases in nucleic acid processing, genome stability and diseases," BioEssays, 2005, pp. 717-729, vol. 27, No. 7.

Shridhar, Viji et al., "A gene from human chromosomal band 3p21.1 encodes a highly conserved arginine-rich protein and is mutated in renal cell carcinomas," Oncogene, 1996, pp. 1931-1939, vol. 12.

Shridhar, Viji et al., "Mutations in the Arginine-rich Protein Gene, in Lung, Breast, and Prostate Cancers, and in Squamous Cell Carcinoma of the Head and Neck," Cancer Research, Dec. 1996, pp. 5576-5578, vol. 56.

Shridhar, Viji et al., "Mutations in the arginine-rich protein gene (ARP) in pancreatic cancer," Oncogene, 1997, pp. 2213-2216, vol. 14.

Tanaka, Hisashiu et al., "Polymorphic variation of the ARP gene on 3p21 in Japanese esophageal cancer patients," Oncology Reports, 2000, pp. 591-593, vol. 7.

Taylor, Todd D. et al., "Human chromosome 11 DNA sequence and analysis including novel gene identification," Nature, Mar. 23, 2006, pp. 497-500, vol. 440.

Tijssen, P., "Preparation of enzyme-antibody or other enzyme-macromolecule conjugates," Practice and Theory of Enzyme Immunoassays, 1985, pp. 221-278, Chapter 11, Elsevier Science Publishers B.V., Amsterdam, The Netherlands.

(56) References Cited

OTHER PUBLICATIONS

Tomida, Mikio et al., "Serum levels of nicotinamide N-methyltransferase in patients with long cancer," Journal of Cancer Research and Clinical Oncology, 2009, pp. 1223-1229, vol. 135.

Yacoub, Adly et al., "The DNA Repair Activity of Human Redox/Repair Protein APE/Ref-1 Is Inactivated by Phosphorylation," Cancer Research, Dec. 1997, pp. 5457-5459, vol. 37.

Zweig, Mark H. and Campbell, Gregory, "Receiver-Operating Characteristic (ROC) Plots: A Fundamental Evaluation Tool in Clinical Medicine," Clinical Chemistry, 1993, pp. 561-577, vol. 39, No. 4.

Kharitonov, Sergei A. et al., "Effects of Corticosteroids on Noninvasive Biomarkers of Inflammation in Asthma and Chronic Obstructive Pulmonary Disease", Proceedings of American Thoracic Society, 2004, vol. 1, pp. 191-199.

Shi, Hui-fang et al., "Clinical significance of CRP in hospitalized patients with acute exacerbations of chronic obstructive pulmonary disease," China Journal of Modern Medicine, May 2008, pp. 1448-1450, vol. 18, No. 10, English abstract.

Zhu, Yehan et al., "Research in change of inflammation markers in sputa of patients with asthma, acute exacerbations of chronic obstructive pulmonary disease (COPD) and its relationship with lung function," Suzhou University Journal of Medical Science, 2005, pp. 317-319, vol. 25, No. 2, English abstract.

GeneCards for ASC Gene, available at http://www.genecards.org/cgi-bin/carddisp.pl?gene=PYCARD, visited website Dec. 24, 2014.

\* cited by examiner

SEQUENCE LISTING

<160> NUMBER OF SEQ ID NOS: 8

<210> SEQ ID NO 1
<211> LENGTH: 195
<212> TYPE: PRT
<213> ORGANISM: Homo sapiens

<400> SEQUENCE: 1

Met Gly Arg Ala Arg Asp Ala Ile Leu Asp Ala Leu Glu Asn Leu Thr
1               5                   10                  15

```
Ala Glu Glu Leu Lys Lys Phe Lys Leu Lys Leu Ser Val Pro Leu
             20                  25                  30

Arg Glu Gly Tyr Gly Arg Ile Pro Arg Gly Ala Leu Leu Ser Met Asp
         35                  40                  45

Ala Leu Asp Leu Thr Asp Lys Leu Val Ser Phe Tyr Leu Glu Thr Tyr
 50                  55                  60

Gly Ala Glu Leu Thr Ala Asn Val Leu Arg Asp Met Gly Leu Gln Glu
 65                  70                  75                  80

Met Ala Gly Gln Leu Gln Ala Ala Thr His Gln Gly Ser Gly Ala Ala
             85                  90                  95

Pro Ala Gly Ile Gln Ala Pro Pro Gln Ser Ala Ala Lys Pro Gly Leu
            100                 105                 110

His Phe Ile Asp Gln His Arg Ala Ala Leu Ile Ala Arg Val Thr Asn
            115                 120                 125

Val Glu Trp Leu Leu Asp Ala Leu Tyr Gly Lys Val Leu Thr Asp Glu
130                 135                 140

Gln Tyr Gln Ala Val Arg Ala Glu Pro Thr Asn Pro Ser Lys Met Arg
145                 150                 155                 160

Lys Leu Phe Ser Phe Thr Pro Ala Trp Asn Trp Thr Cys Lys Asp Leu
            165                 170                 175

Leu Leu Gln Ala Leu Arg Glu Ser Gln Ser Tyr Leu Val Glu Asp Leu
            180                 185                 190

Glu Arg Ser
     195

<210> SEQ ID NO 2
<211> LENGTH: 179
<212> TYPE: PRT
<213> ORGANISM: Homo sapiens

<400> SEQUENCE: 2

Met Trp Ala Thr Gln Gly Leu Ala Val Ala Leu Ala Leu Ser Val Leu
 1               5                  10                  15

Pro Gly Ser Arg Ala Leu Arg Pro Gly Asp Cys Glu Val Cys Ile Ser
             20                  25                  30

Tyr Leu Gly Arg Phe Tyr Gln Asp Leu Lys Asp Arg Asp Val Thr Phe
         35                  40                  45

Ser Pro Ala Thr Ile Glu Asn Glu Leu Ile Lys Phe Cys Arg Glu Ala
 50                  55                  60

Arg Gly Lys Glu Asn Arg Leu Cys Tyr Tyr Ile Gly Ala Thr Asp Asp
 65                  70                  75                  80

Ala Ala Thr Lys Ile Ile Asn Glu Val Ser Lys Pro Leu Ala His His
             85                  90                  95

Ile Pro Val Glu Lys Ile Cys Glu Lys Leu Lys Lys Lys Asp Ser Gln
            100                 105                 110

Ile Cys Glu Leu Lys Tyr Asp Lys Gln Ile Asp Leu Ser Thr Val Asp
            115                 120                 125

Leu Lys Lys Leu Arg Val Lys Glu Leu Lys Lys Ile Leu Asp Asp Trp
130                 135                 140

Gly Glu Thr Cys Lys Gly Cys Ala Glu Lys Ser Asp Tyr Ile Arg Lys
145                 150                 155                 160

Ile Asn Glu Leu Met Pro Lys Tyr Ala Pro Lys Ala Ala Ser Ala Arg
            165                 170                 175

Thr Asp Leu
```

<210> SEQ ID NO 3
<211> LENGTH: 264
<212> TYPE: PRT
<213> ORGANISM: Homo sapiens

<400> SEQUENCE: 3

Met Glu Ser Gly Phe Thr Ser Lys Asp Thr Tyr Leu Ser His Phe Asn
1               5                   10                  15

Pro Arg Asp Tyr Leu Glu Lys Tyr Tyr Lys Phe Gly Ser Arg His Ser
            20                  25                  30

Ala Glu Ser Gln Ile Leu Lys His Leu Leu Lys Asn Leu Phe Lys Ile
        35                  40                  45

Phe Cys Leu Asp Gly Val Lys Gly Asp Leu Leu Ile Asp Ile Gly Ser
    50                  55                  60

Gly Pro Thr Ile Tyr Gln Leu Leu Ser Ala Cys Glu Ser Phe Lys Glu
65                  70                  75                  80

Ile Val Val Thr Asp Tyr Ser Asp Gln Asn Leu Gln Glu Leu Glu Lys
                85                  90                  95

Trp Leu Lys Lys Glu Pro Glu Ala Phe Asp Trp Ser Pro Val Val Thr
            100                 105                 110

Tyr Val Cys Asp Leu Glu Gly Asn Arg Val Lys Gly Pro Glu Lys Glu
        115                 120                 125

Glu Lys Leu Arg Gln Ala Val Lys Gln Val Leu Lys Cys Asp Val Thr
    130                 135                 140

Gln Ser Gln Pro Leu Gly Ala Val Pro Leu Pro Pro Ala Asp Cys Val
145                 150                 155                 160

Leu Ser Thr Leu Cys Leu Asp Ala Ala Cys Pro Asp Leu Pro Thr Tyr
                165                 170                 175

Cys Arg Ala Leu Arg Asn Leu Gly Ser Leu Leu Lys Pro Gly Gly Phe
            180                 185                 190

Leu Val Ile Met Asp Ala Leu Lys Ser Ser Tyr Tyr Met Ile Gly Glu
        195                 200                 205

Gln Lys Phe Ser Ser Leu Pro Leu Gly Arg Glu Ala Val Glu Ala Ala
    210                 215                 220

Val Lys Glu Ala Gly Tyr Thr Ile Glu Trp Phe Glu Val Ile Ser Gln
225                 230                 235                 240

Ser Tyr Ser Ser Thr Met Ala Asn Asn Glu Gly Leu Phe Ser Leu Val
                245                 250                 255

Ala Arg Lys Leu Ser Arg Pro Leu
            260

<210> SEQ ID NO 4
<211> LENGTH: 380
<212> TYPE: PRT
<213> ORGANISM: Homo sapiens

<400> SEQUENCE: 4

Met Gly Ile Gln Gly Leu Ala Lys Leu Ile Ala Asp Val Ala Pro Ser
1               5                   10                  15

Ala Ile Arg Glu Asn Asp Ile Lys Ser Tyr Phe Gly Arg Lys Val Ala
            20                  25                  30

Ile Asp Ala Ser Met Ser Ile Tyr Gln Phe Leu Ile Ala Val Arg Gln
        35                  40                  45

Gly Gly Asp Val Leu Gln Asn Glu Glu Gly Glu Thr Thr Ser His Leu
    50                  55                  60

-continued

```
Met Gly Met Phe Tyr Arg Thr Ile Arg Met Met Glu Asn Gly Ile Lys
 65                  70                  75                  80

Pro Val Tyr Val Phe Asp Gly Lys Pro Pro Gln Leu Lys Ser Gly Glu
                 85                  90                  95

Leu Ala Lys Arg Ser Glu Arg Arg Ala Glu Ala Glu Lys Gln Leu Gln
            100                 105                 110

Gln Ala Gln Ala Ala Gly Ala Glu Gln Glu Val Glu Lys Phe Thr Lys
        115                 120                 125

Arg Leu Val Lys Val Thr Lys Gln His Asn Asp Glu Cys Lys His Leu
130                 135                 140

Leu Ser Leu Met Gly Ile Pro Tyr Leu Asp Ala Pro Ser Glu Ala Glu
145                 150                 155                 160

Ala Ser Cys Ala Ala Leu Val Lys Ala Gly Lys Val Tyr Ala Ala Ala
                165                 170                 175

Thr Glu Asp Met Asp Cys Leu Thr Phe Gly Ser Pro Val Leu Met Arg
            180                 185                 190

His Leu Thr Ala Ser Glu Ala Lys Lys Leu Pro Ile Gln Glu Phe His
        195                 200                 205

Leu Ser Arg Ile Leu Gln Glu Leu Gly Leu Asn Gln Glu Gln Phe Val
    210                 215                 220

Asp Leu Cys Ile Leu Leu Gly Ser Asp Tyr Cys Glu Ser Ile Arg Gly
225                 230                 235                 240

Ile Gly Pro Lys Arg Ala Val Asp Leu Ile Gln Lys His Lys Ser Ile
                245                 250                 255

Glu Glu Ile Val Arg Arg Leu Asp Pro Asn Lys Tyr Pro Val Pro Glu
            260                 265                 270

Asn Trp Leu His Lys Glu Ala His Gln Leu Phe Leu Glu Pro Glu Val
        275                 280                 285

Leu Asp Pro Glu Ser Val Glu Leu Lys Trp Ser Glu Pro Asn Glu Glu
    290                 295                 300

Glu Leu Ile Lys Phe Met Cys Gly Glu Lys Gln Phe Ser Glu Glu Arg
305                 310                 315                 320

Ile Arg Ser Gly Val Lys Arg Leu Ser Lys Ser Arg Gln Gly Ser Thr
                325                 330                 335

Gln Gly Arg Leu Asp Asp Phe Phe Lys Val Thr Gly Ser Leu Ser Ser
            340                 345                 350

Ala Lys Arg Lys Glu Pro Glu Pro Lys Gly Ser Thr Lys Lys Lys Ala
        355                 360                 365

Lys Thr Gly Ala Ala Gly Lys Phe Lys Arg Gly Lys
370                 375                 380

<210> SEQ ID NO 5
<211> LENGTH: 318
<212> TYPE: PRT
<213> ORGANISM: Homo sapiens

<400> SEQUENCE: 5

Met Pro Lys Arg Gly Lys Lys Gly Ala Val Ala Glu Asp Gly Asp Glu
  1               5                  10                  15

Leu Arg Thr Glu Pro Glu Ala Lys Ser Lys Thr Ala Ala Lys Lys
             20                  25                  30

Asn Asp Lys Glu Ala Ala Gly Glu Gly Pro Ala Leu Tyr Glu Asp Pro
         35                  40                  45

Pro Asp Gln Lys Thr Ser Pro Ser Gly Lys Pro Ala Thr Leu Lys Ile
     50                  55                  60
```

Cys Ser Trp Asn Val Asp Gly Leu Arg Ala Trp Ile Lys Lys Gly
 65                  70                  75                  80

Leu Asp Trp Val Lys Glu Ala Pro Asp Ile Leu Cys Leu Gln Glu
                 85                  90                  95

Thr Lys Cys Ser Glu Asn Lys Leu Pro Ala Glu Leu Gln Glu Leu Pro
            100                 105                 110

Gly Leu Ser His Gln Tyr Trp Ser Ala Pro Ser Asp Lys Glu Gly Tyr
            115                 120                 125

Ser Gly Val Gly Leu Leu Ser Arg Gln Cys Pro Leu Lys Val Ser Tyr
130                 135                 140

Gly Ile Gly Asp Glu His Asp Gln Glu Gly Arg Val Ile Val Ala
145                 150                 155                 160

Glu Phe Asp Ser Phe Val Leu Val Thr Ala Tyr Val Pro Asn Ala Gly
                165                 170                 175

Arg Gly Leu Val Arg Leu Glu Tyr Arg Gln Arg Trp Asp Glu Ala Phe
            180                 185                 190

Arg Lys Phe Leu Lys Gly Leu Ala Ser Arg Lys Pro Leu Val Leu Cys
            195                 200                 205

Gly Asp Leu Asn Val Ala His Glu Glu Ile Asp Leu Arg Asn Pro Lys
210                 215                 220

Gly Asn Lys Lys Asn Ala Gly Phe Thr Pro Gln Glu Arg Gln Gly Phe
225                 230                 235                 240

Gly Glu Leu Leu Gln Ala Val Pro Leu Ala Asp Ser Phe Arg His Leu
                245                 250                 255

Tyr Pro Asn Thr Pro Tyr Ala Tyr Thr Phe Trp Thr Tyr Met Met Asn
            260                 265                 270

Ala Arg Ser Lys Asn Val Gly Trp Arg Leu Asp Tyr Phe Leu Leu Ser
            275                 280                 285

His Ser Leu Leu Pro Ala Leu Cys Asp Ser Lys Ile Arg Ser Lys Ala
290                 295                 300

Leu Gly Ser Asp His Cys Pro Ile Thr Leu Tyr Leu Ala Leu
305                 310                 315

<210> SEQ ID NO 6
<211> LENGTH: 760
<212> TYPE: PRT
<213> ORGANISM: Homo sapiens

<400> SEQUENCE: 6

Met Lys Thr Trp Val Lys Ile Val Phe Gly Val Ala Thr Ser Ala Val
1               5                   10                  15

Leu Ala Leu Leu Val Met Cys Ile Val Leu Arg Pro Ser Arg Val His
                20                  25                  30

Asn Ser Glu Glu Asn Thr Met Arg Ala Leu Thr Leu Lys Asp Ile Leu
            35                  40                  45

Asn Gly Thr Phe Ser Tyr Lys Thr Phe Phe Pro Asn Trp Ile Ser Gly
        50                  55                  60

Gln Glu Tyr Leu His Gln Ser Ala Asp Asn Asn Ile Val Leu Tyr Asn
65                  70                  75                  80

Ile Glu Thr Gly Gln Ser Tyr Thr Ile Leu Ser Asn Arg Thr Met Lys
                85                  90                  95

Ser Val Asn Ala Ser Asn Tyr Gly Leu Ser Pro Asp Arg Gln Phe Val
            100                 105                 110

Tyr Leu Glu Ser Asp Tyr Ser Lys Leu Trp Arg Tyr Ser Tyr Thr Ala

```
                115                 120                 125
Thr Tyr Tyr Ile Tyr Asp Leu Ser Asn Gly Glu Phe Val Arg Gly Asn
130                 135                 140

Glu Leu Pro Arg Pro Ile Gln Tyr Leu Cys Trp Ser Pro Val Gly Ser
145                 150                 155                 160

Lys Leu Ala Tyr Val Tyr Gln Asn Asn Ile Tyr Leu Lys Gln Arg Pro
                165                 170                 175

Gly Asp Pro Pro Phe Gln Ile Thr Phe Asn Gly Arg Glu Asn Lys Ile
            180                 185                 190

Phe Asn Gly Ile Pro Asp Trp Val Tyr Glu Glu Met Leu Ala Thr
        195                 200                 205

Lys Tyr Ala Leu Trp Trp Ser Pro Asn Gly Lys Phe Leu Ala Tyr Ala
210                 215                 220

Glu Phe Asn Asp Thr Asp Ile Pro Val Ile Ala Tyr Ser Tyr Tyr Gly
225                 230                 235                 240

Asp Glu Gln Tyr Pro Arg Thr Ile Asn Ile Pro Tyr Pro Lys Ala Gly
                245                 250                 255

Ala Lys Asn Pro Val Val Arg Ile Phe Ile Ile Asp Thr Thr Tyr Pro
            260                 265                 270

Ala Tyr Val Gly Pro Gln Glu Val Pro Val Pro Ala Met Ile Ala Ser
        275                 280                 285

Ser Asp Tyr Tyr Phe Ser Trp Leu Thr Trp Val Thr Asp Glu Arg Val
290                 295                 300

Cys Leu Gln Trp Leu Lys Arg Val Gln Asn Val Ser Val Leu Ser Ile
305                 310                 315                 320

Cys Asp Phe Arg Glu Asp Trp Gln Thr Trp Asp Cys Pro Lys Thr Gln
                325                 330                 335

Glu His Ile Glu Glu Ser Arg Thr Gly Trp Ala Gly Gly Phe Phe Val
            340                 345                 350

Ser Thr Pro Val Phe Ser Tyr Asp Ala Ile Ser Tyr Tyr Lys Ile Phe
        355                 360                 365

Ser Asp Lys Asp Gly Tyr Lys His Ile His Tyr Ile Lys Asp Thr Val
370                 375                 380

Glu Asn Ala Ile Gln Ile Thr Ser Gly Lys Trp Glu Ala Ile Asn Ile
385                 390                 395                 400

Phe Arg Val Thr Gln Asp Ser Leu Phe Tyr Ser Ser Asn Glu Phe Glu
                405                 410                 415

Glu Tyr Pro Gly Arg Arg Asn Ile Tyr Arg Ile Ser Ile Gly Ser Tyr
            420                 425                 430

Pro Pro Ser Lys Lys Cys Val Thr Cys His Leu Arg Lys Glu Arg Cys
        435                 440                 445

Gln Tyr Tyr Thr Ala Ser Phe Ser Asp Tyr Ala Lys Tyr Tyr Ala Leu
450                 455                 460

Val Cys Tyr Gly Pro Gly Ile Pro Ile Ser Thr Leu His Asp Gly Arg
465                 470                 475                 480

Thr Asp Gln Glu Ile Lys Ile Leu Glu Glu Asn Lys Glu Leu Glu Asn
                485                 490                 495

Ala Leu Lys Asn Ile Gln Leu Pro Lys Glu Glu Ile Lys Lys Leu Glu
            500                 505                 510

Val Asp Glu Ile Thr Leu Trp Tyr Lys Met Ile Leu Pro Pro Gln Phe
        515                 520                 525

Asp Arg Ser Lys Lys Tyr Pro Leu Leu Ile Gln Val Tyr Gly Gly Pro
530                 535                 540
```

```
Cys Ser Gln Ser Val Arg Ser Phe Ala Val Asn Trp Ile Ser Tyr
545                 550                 555                 560

Leu Ala Ser Lys Glu Gly Met Val Ile Ala Leu Val Asp Gly Arg Gly
                565                 570                 575

Thr Ala Phe Gln Gly Asp Lys Leu Leu Tyr Ala Val Tyr Arg Lys Leu
            580                 585                 590

Gly Val Tyr Glu Val Glu Asp Gln Ile Thr Ala Val Arg Lys Phe Ile
                595                 600                 605

Glu Met Gly Phe Ile Asp Glu Lys Arg Ile Ala Ile Trp Gly Trp Ser
        610                 615                 620

Tyr Gly Gly Tyr Val Ser Ser Leu Ala Leu Ala Ser Gly Thr Gly Leu
625                 630                 635                 640

Phe Lys Cys Gly Ile Ala Val Ala Pro Val Ser Ser Trp Glu Tyr Tyr
                645                 650                 655

Ala Ser Val Tyr Thr Glu Arg Phe Met Gly Leu Pro Thr Lys Asp Asp
                660                 665                 670

Asn Leu Glu His Tyr Lys Asn Ser Thr Val Met Ala Arg Ala Glu Tyr
            675                 680                 685

Phe Arg Asn Val Asp Tyr Leu Leu Ile His Gly Thr Ala Asp Asp Asn
        690                 695                 700

Val His Phe Gln Asn Ser Ala Gln Ile Ala Lys Ala Leu Val Asn Ala
705                 710                 715                 720

Gln Val Asp Phe Gln Ala Met Trp Tyr Ser Asp Gln Asn His Gly Leu
                725                 730                 735

Ser Gly Leu Ser Thr Asn His Leu Tyr Thr His Met Thr His Phe Leu
            740                 745                 750

Lys Gln Cys Phe Ser Leu Ser Asp
                755                 760

<210> SEQ ID NO 7
<211> LENGTH: 766
<212> TYPE: PRT
<213> ORGANISM: Homo sapiens

<400> SEQUENCE: 7

Met Lys Thr Pro Trp Lys Val Leu Leu Gly Leu Leu Gly Ala Ala Ala
1               5                   10                  15

Leu Val Thr Ile Ile Thr Val Pro Val Val Leu Leu Asn Lys Gly Thr
                20                  25                  30

Asp Asp Ala Thr Ala Asp Ser Arg Lys Thr Tyr Thr Leu Thr Asp Tyr
            35                  40                  45

Leu Lys Asn Thr Tyr Arg Leu Lys Leu Tyr Ser Leu Arg Trp Ile Ser
        50                  55                  60

Asp His Glu Tyr Leu Tyr Lys Gln Glu Asn Asn Ile Leu Val Phe Asn
65                  70                  75                  80

Ala Glu Tyr Gly Asn Ser Ser Val Phe Leu Glu Asn Ser Thr Phe Asp
                85                  90                  95

Glu Phe Gly His Ser Ile Asn Asp Tyr Ser Ile Ser Pro Asp Gly Gln
            100                 105                 110

Phe Ile Leu Leu Glu Tyr Asn Tyr Val Lys Gln Trp Arg His Ser Tyr
        115                 120                 125

Thr Ala Ser Tyr Asp Ile Tyr Asp Leu Asn Lys Arg Gln Leu Ile Thr
    130                 135                 140

Glu Glu Arg Ile Pro Asn Asn Thr Gln Trp Val Thr Trp Ser Pro Val
```

```
        145                 150                 155                 160
Gly His Lys Leu Ala Tyr Val Trp Asn Asn Asp Ile Tyr Val Lys Ile
                    165                 170                 175

Glu Pro Asn Leu Pro Ser Tyr Arg Ile Thr Trp Thr Gly Lys Glu Asp
            180                 185                 190

Ile Ile Tyr Asn Gly Ile Thr Asp Trp Val Tyr Glu Glu Val Phe
        195                 200                 205

Ser Ala Tyr Ser Ala Leu Trp Trp Ser Pro Asn Gly Thr Phe Leu Ala
210                 215                 220

Tyr Ala Gln Phe Asn Asp Thr Glu Val Pro Leu Ile Glu Tyr Ser Phe
225                 230                 235                 240

Tyr Ser Asp Glu Ser Leu Gln Tyr Pro Lys Thr Val Arg Val Pro Tyr
                245                 250                 255

Pro Lys Ala Gly Ala Val Asn Pro Thr Val Lys Phe Phe Val Val Asn
            260                 265                 270

Thr Asp Ser Leu Ser Ser Val Thr Asn Ala Thr Ser Ile Gln Ile Thr
        275                 280                 285

Ala Pro Ala Ser Met Leu Ile Gly Asp His Tyr Leu Cys Asp Val Thr
    290                 295                 300

Trp Ala Thr Gln Glu Arg Ile Ser Leu Gln Trp Leu Arg Arg Ile Gln
305                 310                 315                 320

Asn Tyr Ser Val Met Asp Ile Cys Asp Tyr Asp Glu Ser Ser Gly Arg
                325                 330                 335

Trp Asn Cys Leu Val Ala Arg Gln His Ile Glu Met Ser Thr Thr Gly
            340                 345                 350

Trp Val Gly Arg Phe Arg Pro Ser Glu Pro His Phe Thr Leu Asp Gly
        355                 360                 365

Asn Ser Phe Tyr Lys Ile Ile Ser Asn Glu Glu Gly Tyr Arg His Ile
    370                 375                 380

Cys Tyr Phe Gln Ile Asp Lys Lys Asp Cys Thr Phe Ile Thr Lys Gly
385                 390                 395                 400

Thr Trp Glu Val Ile Gly Ile Glu Ala Leu Thr Ser Asp Tyr Leu Tyr
                405                 410                 415

Tyr Ile Ser Asn Glu Tyr Lys Gly Met Pro Gly Gly Arg Asn Leu Tyr
            420                 425                 430

Lys Ile Gln Leu Ser Asp Tyr Thr Lys Val Thr Cys Leu Ser Cys Glu
        435                 440                 445

Leu Asn Pro Glu Arg Cys Gln Tyr Tyr Ser Val Ser Phe Ser Lys Glu
    450                 455                 460

Ala Lys Tyr Tyr Gln Leu Arg Cys Ser Gly Pro Gly Leu Pro Leu Tyr
465                 470                 475                 480

Thr Leu His Ser Ser Val Asn Asp Lys Gly Leu Arg Val Leu Glu Asp
                485                 490                 495

Asn Ser Ala Leu Asp Lys Met Leu Gln Asn Val Gln Met Pro Ser Lys
            500                 505                 510

Lys Leu Asp Phe Ile Ile Leu Asn Glu Thr Lys Phe Trp Tyr Gln Met
        515                 520                 525

Ile Leu Pro Pro His Phe Asp Lys Ser Lys Lys Tyr Pro Leu Leu Leu
    530                 535                 540

Asp Val Tyr Ala Gly Pro Cys Ser Gln Lys Ala Asp Thr Val Phe Arg
545                 550                 555                 560

Leu Asn Trp Ala Thr Tyr Leu Ala Ser Thr Glu Asn Ile Ile Val Ala
                565                 570                 575
```

```
Ser Phe Asp Gly Arg Gly Ser Gly Tyr Gln Gly Asp Lys Ile Met His
            580                 585                 590

Ala Ile Asn Arg Arg Leu Gly Thr Phe Glu Val Glu Asp Gln Ile Glu
        595                 600                 605

Ala Ala Arg Gln Phe Ser Lys Met Gly Phe Val Asp Asn Lys Arg Ile
    610                 615                 620

Ala Ile Trp Gly Trp Ser Tyr Gly Gly Tyr Val Thr Ser Met Val Leu
625                 630                 635                 640

Gly Ser Gly Ser Gly Val Phe Lys Cys Gly Ile Ala Val Ala Pro Val
                645                 650                 655

Ser Arg Trp Glu Tyr Tyr Asp Ser Val Tyr Thr Glu Arg Tyr Met Gly
            660                 665                 670

Leu Pro Thr Pro Glu Asp Asn Leu Asp His Tyr Arg Asn Ser Thr Val
            675                 680                 685

Met Ser Arg Ala Glu Asn Phe Lys Gln Val Glu Tyr Leu Leu Ile His
        690                 695                 700

Gly Thr Ala Asp Asp Asn Val His Phe Gln Gln Ser Ala Gln Ile Ser
705                 710                 715                 720

Lys Ala Leu Val Asp Val Gly Val Asp Phe Gln Ala Met Trp Tyr Thr
                725                 730                 735

Asp Glu Asp His Gly Ile Ala Ser Ser Thr Ala His Gln His Ile Tyr
            740                 745                 750

Thr His Met Ser His Phe Ile Lys Gln Cys Phe Ser Leu Pro
            755                 760                 765

<210> SEQ ID NO 8
<211> LENGTH: 14
<212> TYPE: PRT
<213> ORGANISM: Artificial Sequence
<220> FEATURE:
<223> OTHER INFORMATION: N-terminal peptide extension

<400> SEQUENCE: 8

Met Arg Gly Ser His His His His His His Ile Glu Gly Arg
1               5                   10
```

ASC AS A MARKER FOR CHRONIC OBSTRUCTIVE PULMONARY DISEASE (COPD)

CROSS-REFERENCE TO RELATED APPLICATIONS

This application is a continuation of International Application No. PCT/EP2012/053847 filed Mar. 7, 2012 which claims the benefit of European Patent Application No. 11157917.3 filed Mar. 11, 2011, the disclosures of which are hereby incorporated by reference in their entirety.

SEQUENCE LISTING

The instant application contains a Sequence Listing which has been submitted in ASCII format via EFS-Web and is hereby incorporated by reference in its entirety. Said ASCII copy, created on Sep. 4, 2013, is named SEQUENCE_LISTING_27346US.txt, and is twenty-five thousand four hundred and one bytes in size.

BACKGROUND

Chronic obstructive pulmonary disease (COPD) is a disease characterized by chronic inflammation and irreversible airflow obstruction with a decline in the lung function parameter FEV1 that is more rapid than normal. This leads to a limitation of the flow of air to and from the lungs causing shortness of breath. The disease has two major aspects of pathology, namely chronic bronchitis, characterized by mucus hyper-secretion from the conducting airways, and emphysema, characterized by destructive changes in the alveoli. In clinical practice, COPD is defined by its characteristically low airflow on lung function tests (Nathell, L., et al., Respiratory Research 8 (2007) 89). In contrast to asthma, this limitation is poorly reversible and usually gets progressively worse over time.

Worldwide, COPD ranked as the sixth leading cause of death in 1990. It is projected to be the fourth leading cause of death worldwide by 2030 due to an increase in smoking rates and demographic changes in many countries (Mathers, C. D., et al., PLoS Med. 3 (2006) e442). COPD is the 4th leading cause of death in the U.S., and the economic burden of COPD in the U.S. in 2007 was $42.6 billion in health care costs and lost productivity.

COPD may be caused by noxious particles or gas, for example from tobacco smoking, which triggers an abnormal inflammatory response in the lung (Rabe, K. F., et al., Am. J. Respir. Crit. Care Med. 176 (2007) 532-555 and Hogg, J. C., et al., N. Engl. J. Med. 350 (2004) 2645-2653). The inflammatory response in the larger airways is known as chronic bronchitis, which is diagnosed clinically when people regularly cough up sputum. In the alveoli, the inflammatory response can cause destruction of the tissues of the lung, a process known as emphysema. The natural course of COPD is characterized by occasional sudden worsening of symptoms called acute exacerbations, which may be caused by infections or air pollution.

Many of the symptoms of COPD are shared by other respiratory diseases such as asthma, bronchitis, pulmonary fibrosis and tuberculosis. The current gold standard for the diagnosis of COPD requires a lung function tests (spirometry), which is a time consuming and costly procedure which can be only realized by a specialized lung physician. A spirometry test, for example, is highly dependent on patient cooperation and effort, and is normally repeated at least three times to ensure reproducibility. In some cases, chronic bronchitis can be diagnosed by asking the patient whether they have a "productive cough" i.e. one that yields sputum.

Asthma differs from COPD in its pathogenic and therapeutic response, and should therefore be considered a different clinical entity. For example, in COPD there is an increase in neutrophils, macrophages and T-lymphocytes (specifically CD8+) in various parts of the lungs is observed, which relate to the degree of airflow limitation (Saetta, M., et al., Am. J. Respir. Crit. Care Med. 157 (1998) 822-826). There may be an increase in eosinophils in some patients, particularly during exacerbations (Saetta, M., et al., Am. J. Respir. Crit. Care Med. 150 (1994) 1646-1652 and Saetta, M., et al., Clin. Exp. Allergy 26 (1996) 766-774). This inflammatory pattern is markedly different from that seen in patients with bronchial asthma. Inflammatory changes may persist after quitting smoking. The mechanisms explaining the perpetuation of this inflammatory response in the absence of the inciting events are unknown.

However, some patients with asthma develop poor reversible airflow limitation, which may be indistinguishable from patients with COPD but for practical purposes are treated as asthma. The high prevalence of asthma and COPD in the general population results in the co-existence of both disease entities in many individuals. This is characterised by significant airflow limitation and a large response to bronchodilators. In these patients, the forced expiratory volume in one second (FEV1) does not return to normal and frequently worsens over time.

SUMMARY OF THE DISCLOSURE

The present disclosure relates to an in vitro method aiding in the assessment of chronic obstructive pulmonary disease (=COPD). It discloses the use of the protein ASC as a marker of COPD. Furthermore, it especially relates to a method for assessing COPD from a sample, derived from an individual by measuring the protein ASC in said sample in vitro.

As disclosed here, It has now been found that the use of protein ASC can at least partially overcome some of the problems of the methods available for assessment of COPD presently known. Surprisingly it was found in the present disclosure that an in vitro determination of the concentration of protein ASC in a sample allows for the assessment of COPD. In this context it was found that an elevated concentration of said protein ASC in such sample obtained from an individual compared to a reference concentration for protein ASC is indicative for the presence of COPD.

Disclosed herein is an in vitro method for assessing COPD comprising determining in a body fluid sample the concentration of protein ASC by an immunological detection method and using the determined result, particularly the concentration determined, in the assessment of COPD.

The disclosure also relates to an in vitro method for assessing chronic obstructive pulmonary disease (COPD) in a subject, comprising a) determining the concentration of protein ASC in a sample, and b) comparing the concentration of protein ASC determined in step (a) with a reference concentration of protein ASC, wherein a concentration of protein ASC above a reference concentration is indicative for COPD.

In a further embodiment the present disclosure relates to the use of the protein ASC in the in vitro assessment of COPD in a sample, wherein a concentration of protein ASC above a reference concentration for protein ASC is indicative for COPD. Further disclosed is the use of a marker panel comprising protein ASC and one or more other marker for COPD in the in vitro assessment of COPD in a sample, wherein a concentration of protein ASC above a reference concentration for protein ASC is indicative for COPD.

In a further embodiment the present disclosure relates to the use of the in vitro method for assessing COPD according to the present disclosure to differentiate COPD from other types of lung diseases, such as asthma.

In a further embodiment the present disclosure relates to a diagnostic device for carrying out the in vitro method for assessing COPD according to the present disclosure.

Also provided is a kit for performing the in vitro method for assessing COPD according to the present disclosure comprising the reagents required to specifically determine the concentration of protein ASC.

Additional aspects and advantages of the present disclosure will be apparent in view of the detailed description which follows. It should be understood, however, that the detailed description and the specific examples, while describing exemplary embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The features of this disclosure, and the manner of attaining them, will become more apparent and the disclosure itself will be better understood by reference to the following description of embodiments of the disclosure taken in conjunction with the accompanying drawing.

Figure 1:
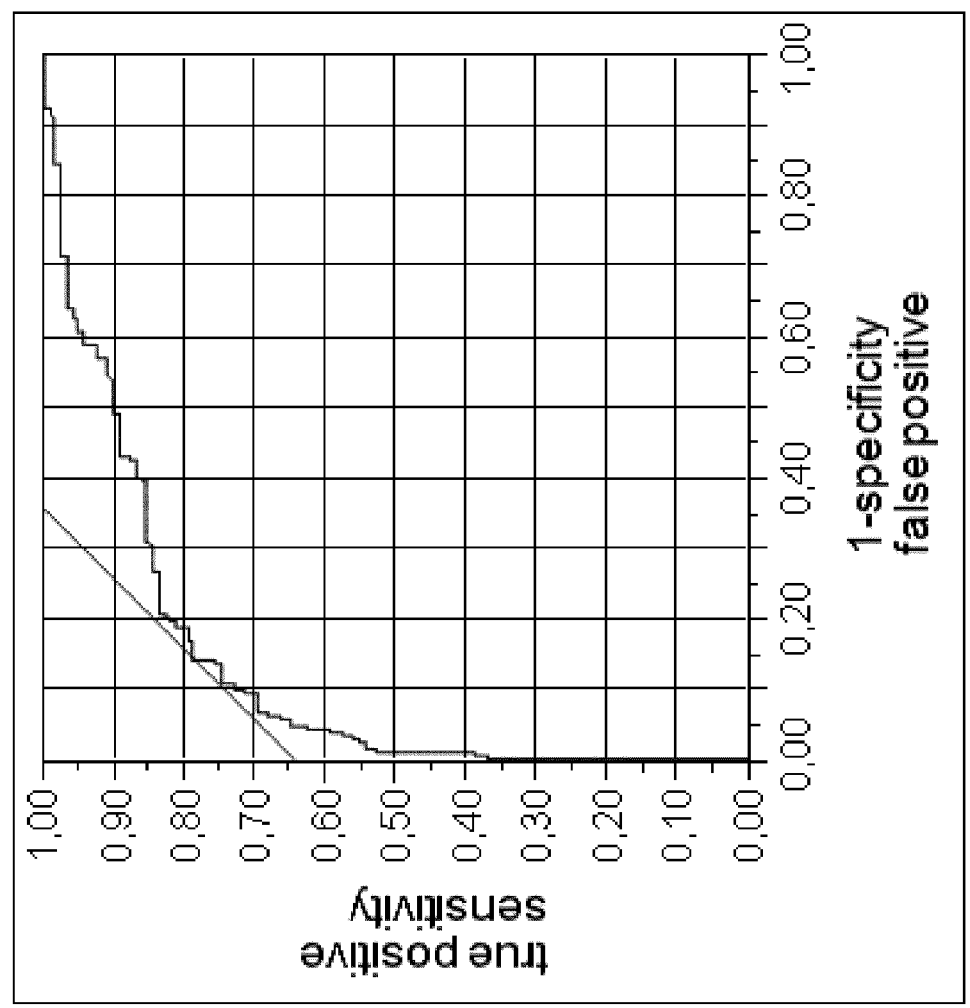
FIG. 1 shows the plot of the receiver operator characteristics (ROC-plot) of protein ASC in COPD samples with an AUC of 0.88 (ROC 88%) for the assessment of 123 samples obtained from patients with COPD as compared to 186 control samples obtained from healthy control patients (X-axis: 1-specificity (false positive); Y-axis: sensitivity (true positive)).

Although the drawings represent embodiments of the present disclosure, the drawings are not necessarily to scale and certain features may be exaggerated in order to better illustrate and explain the present disclosure. The exemplifications set out herein illustrate an exemplary embodiment of the disclosure, in one form, and such exemplifications are not to be construed as limiting the scope of the disclosure in any manner.

BRIEF DESCRIPTION OF THE SEQUENCE LISTING

SEQ ID NO.1: is the amino acid sequence of the human protein ASC (SwissProt database accession number: Q9ULZ3).

SEQ ID NO.2: is the amino acid sequence of the human protein ARMET (SwissProt database accession number: P55145).

SEQ ID NO.3: is the amino acid sequence of the human protein NNMT (SwissProt database accession number: P40261).

SEQ ID NO.4: is the amino acid sequence of the human protein FEN1 (SwissProt database accession number: P39748).

SEQ ID NO.5: is the amino acid sequence of the human protein APEX1 (SwissProt database accession number: P27695).

SEQ ID NO.6: is the amino acid sequence of the human protein Seprase (SwissProt database accession number: Q12884).

SEQ ID NO.7: is the amino acid sequence of the human protein DPPIV (SwissProt database accession number: P27487).

SEQ ID NO.8: is the N-terminal peptide extension.

Although the sequence listing represents an embodiment of the present disclosure, the sequence listing is not to be construed as limiting the scope of the disclosure in any manner and may be modified in any manner as consistent with the instant disclosure and as set forth herein.

DETAILED DESCRIPTION OF THE DISCLOSURE

The embodiments disclosed herein are not intended to be exhaustive or limit the disclosure to the precise form disclosed in the following detailed description. Rather, the embodiments are chosen and described so that others skilled in the art may utilize their teachings.

The inventors of the present disclosure have surprisingly been able to demonstrate that the marker protein ASC is useful in the assessment of COPD. Due to the uncertainties of classifying the various stages of lung damage, and especially of COPD by state of the art methods, it may well be that the protein ASC may become one of the pivotal criteria in the assessment of patients with COPD in the future. The present disclosure provides a simple and cost-efficient procedure of COPD assessments, e.g. to identify individuals suspected of having COPD. For this purpose, a general COPD marker present in the circulation which is detectable in body fluids (e.g. blood, serum or plasma) is utilized.

Whole blood, serum or plasma are the most widely used sources of sample in clinical routine. The identification of an early COPD marker that would aid in the reliable COPD detection or provide early prognostic information could lead to a method that would greatly aid in the diagnosis and in the management of this disease. It is especially important to improve the early diagnosis of COPD, since for patients diagnosed in early stages of COPD the chances of reversibility of lung damages are much higher as compared to those patients diagnosed at a more progressed stage of disease.

The instant disclosure provides a reliable and straightforward indicator of the COPD disease state (for example, a surrogate marker) both in order to reliably distinguish the symptoms of COPD from those of the above mentioned other respiratory diseases, to predict changes in disease severity, disease progression and response to medicine. The diagnostic sensitivity or specificity of a test according to the instant disclosure a test can be assessed by its receiver-operating characteristics, which is described in detail below.

The method of the present disclosure is suitable for the assessment of COPD. Increased concentrations of protein ASC in a sample as compared to normal controls have been found to be indicative of COPD.

In one embodiment the present disclosure relates to an in vitro method for assessing chronic obstructive pulmonary disease (COPD) in a subject, comprising a) determining the concentration of protein ASC in a sample, and b) comparing the concentration of protein ASC determined in step (a) with a reference concentration of protein ASC, wherein a concentration of protein ASC above a reference concentration is indicative for COPD.

In a further embodiment the present disclosure relates to an in vitro method for assessing chronic obstructive pulmonary disease (COPD) in a subject, comprising a) determining the concentration of protein ASC in a body fluid sample, and b) comparing the concentration of protein ASC determined in step (a) with a reference concentration of protein ASC, wherein a concentration of protein ASC above a reference concentration is indicative for the presence of COPD.

ASC, the "apoptosis-associated speck-like protein containing a caspase-associated recruitment domain" is also known as "target of methylation-induced silencing 1" (TMS1) (Swiss-PROT: Q9ULZ3). The ASC protein in the sense of the present disclosure, characterized by the sequence given in SEQ ID NO:1, is a 22 kDa protein. Caspase-associated recruitment domains (CARDs) mediate the interaction between adaptor proteins such as APAF1 (apoptotic protease activating factor 1) and the pro-form of caspases (e.g., CASP 9) participating in apoptosis. ASC is a member of the CARD-containing adaptor protein family. In WO 2006/105252 is has been shown, that the gene expression level of ASC (=CARD-9) is indicative for the diagnosis of COPD.

The biological role and function of ARMET (arginine-rich, mutated in early stage tumors, ARP, Swiss-PROT ID: P55145) protein remains largely elusive. The ARMET protein in the sense of the present disclosure, characterized by the sequence given in SEQ ID NO:2, is a 20.3 kDa protein. The ARMET protein consists of 179 amino acids, and carries a predicted signal sequence (aa 1-21). The corresponding gene is located in chromosomal band 3p21.1 and was first characterized by Shridhar, V., et al., (Oncogene 12 (1996) 1931-1939). The gene is highly conserved and can be found many mammalian species, like rat, mouse, cow, and hamster. ARMET was named as such, because initial studies suggested ARMET to be 50 amino acids longer at the N-terminus carrying an arginine-rich region (Shridhar, V., et al., Oncogene 12 (1996) 1931-1939; Shridhar, R., et al., Cancer Res. 56 (1996) 5576-5578; Shridhar, V., et al., Oncogene 14 (1997) 2213-2216). However, more recent studies indicate transcribed evidence for a smaller open reading frame that does not encode the arginine tract (Tanaka, H., et al., Oncol. Rep. 7 (2000) 591-593; Mizobuchi, N., et al., Cell Struct. Funct. 32 (2007) 41-50). With the corresponding protein size correction, the initially described mutated codon (ATG50) is now identified to be the initiation codon. Petrova, P., et al., (J. Mol. Neurosci. 20 (2003) 173-188) purified the ARMET gene product from conditioned medium of a rat mesencephalic type-1 astrocyte cell line and named it MANF (Mensencephalic Astrocyte-derived Neurotrophic Factor). Most recent studies demonstrated that ARMET is upregulated by the "unfolded protein response" (UPR), a process which is activated once misfolded proteins accumulate in the endoplasmatic reticulum (ER) (Tanaka, H., et al., Oncol. Rep. 7 (2000) 591-593; Apostolou, A., et al., Exp. Cell Res. 314 (2008) 2454-2467). Based on this study ARMET is characterized as a novel secreted mediator of the adaptive pathway of UPR.

The NNMT (nicotinamide N-methyltransferase; Swiss-PROT: P40261) protein in the sense of the present disclosure, characterized by the sequence given in SEQ ID NO:3, is a 29.6 kDa protein and has an isoelectric point of 5.56. NNMT catalyzes the N-methylation of nicotinamide and other pyridines. This activity is important for biotransformation of many drugs and xenobiotic compounds. The protein has been reported to be predominantly expressed in liver and is located in the cytoplasm. NNMT has been cloned from cDNA from human liver and contained a 792-nucleotide open reading frame that encoded a 264-amino acid protein with a calculated molecular mass of 29.6 kDa. (Aksoy, S., et al., J. Biol. Chem. 269 (1994) 14835-14840). Little is known in the literature about a potential role of the enzyme in human COPD. In the Am. J. of Respiratory and Critical Care Medicine vol. 181 (No. 8), 798-805 a higher mRNA expression of NNMT in skeletal muscle cells of COPD patients has been observed. In a study it has been shown that NNMT is a useful biomarker for lung cancer (LC) (J. of Cancer Res. and Clin. One. vol. 136, no. 9, (2009) 1223.1229). In said study it has been found that serum levels of NNMT were significantly higher in LC patients than in COPD patients and healthy donors.

Flap endonuclease-1 protein (=FEN1, FEN-1), Swiss-PROT ID: P39748 in the sense of the present disclosure, is a nuclear protein of 380 amino acids with a molecular weight of 42.6 kDa, characterized by the sequence given in SEQ ID NO:4. The coding sequence of human FEN1 was predicted by Murray in 1994 (Murray, J. M., et al., Mol. Cell. Biol. 14 (1994) 4878-4888) from a newly cloned sequence. Based on the function of the yeast homolog rad2 a function in high fidelity chromosome segregation and in the repair of UV-induced DNA damage was suggested. As these are fundamental processes in chromosomal integrity, the authors also proposed an involvement of the protein in cancer avoidance. The gene locus on human chromosome 11 was later identified by Hiraoka, et al., (Hiraoka L. R., et al., Genomics 25 (1995) 220-225) and Taylor, et al., (Taylor, T. D., et al., Nature 440 (2006) 497-500). The functions of FEN1 and its interactions with DNA have been the focus of numerous studies (Robins, P., et al., J. Biol. Chem. 269 (1994) 28535-28538), Shen, B., et al., J. Biol. Chem. 271 (1996) 9173-9176; Hasan, S., et al., Mol. Cell. 7 (2001) 1221-1231; Qiu, J., et al., J. Biol. Chem. 277 (2002) 24659-24666 and Sakurai, S., et al., EMBO J. 24

(2005) 683-693). Several enzymatic functions in DNA metabolism have been demonstrated including endonuclease activity that cleaves the 5'-overhanging flap structure generated by displacement synthesis when DNA polymerase encounters the 5'-end of a downstream Okazaki fragment. Additionally FEN1 also possesses a 5' to 3' exonuclease activity on niked or gapped double-stranded DNA, and exhibits RNase H activity. These have been reviewed by Shen et al. (Shen, B., et al., BioEssays 27 (2005) 717-729) or Liu, et al., (Liu, Y., et al., Annu. Rev. Biochem. 73 (2004) 589-615).

The AP endonuclease (APEX1, APEX-1) (Swiss-Prot. P27695) in the sense of the present disclosure is characterized by the sequence given in SEQ ID NO:5. The unprocessed precursor molecule consists of 318 amino acids and has a molecular weight of 35.6 kDa. APEX1 is involved in DNA repair and excises the apurinic or apyrimidinic site of DNA strands. Such abasic sites are relative frequently generated either spontaneously or through chemical agents or by DNA glycosylases that remove specific abnormal bases.

AP sites are pre-mutagenic lesions that can prevent normal DNA replication so the cell contains systems to identify and repair such sites. (Barzilay, G., and Hickson, I. D., Bioessays 17 (1995) 713-719). The 3D structure was elucidated and the amino acids involved in endonuclease activity were identified (Barizilay, G., et al., Nature Structural Biology 2 (1995) 561-567; Gorman, M. A., et al., EMBO Journal 16 (1997) 6548-6558; Beernink, P., et al., J. Mol. Biol. 307 (2001) 1023-1034). APEX1 is also a redox regulator of various transcription factors such as c-Fos, c-Jun, NF-KB and HIF-1. This activity seems to be independent from the endonuclease activity. Both functions are located on different domains of the protein (Barzilay, G., and Hickson, I. D., Bioessays 17 (1995) 713-719). Phosphorylation of APEX1 by protein kinase C increases redox activity whereas the unphosphorylated form is involved in DNA-repair (Yacoub, A., et al., Cancer Res. 57 (1997) 5457-5459). One phosphorylation site, Y 261, (according to the Swissprot sequence) was identified by Rush, J., et al., Nature Biotech. 23 (2005) 94-101).

Seprase, also known as fibroblast activation protein (=FAP), in the sense of the present disclosure is as a 170 kDa glycoprotein having gelatinase and dipeptidyl peptidase activity consisting of two identical monomeric Seprase units (Pineiro-Sanchez, M. L., et al., J. Biol. Chem. 272 (1997) 7595-7601; Park, J. E., et al., J. Biol. Chem. 274 (1999) 36505-36512). The monomer of the human membrane bound Seprase protein comprises 760 amino acids and is shown in SEQ ID NO: 6. Human Seprase is predicted to have its first 4 N-terminal residues within the fibroblast cytoplasm, followed by a 21-residue transmembrane domain and then a 734 residue extracellular C-terminal catalytic domain (Goldstein, L. A., et al., Biochim. Biophys. Acta. 1361 (1997) 11-19; Scanlan, M. J., et al., Proc. Natl. Acad. Sci. USA 91 (1994) 5657-5661). A shorter form of human Seprase protein is known to a person skilled in the art as soluble Seprase or circulating antiplasmin-cleaving enzyme (=APCE) (Lee, K. N., et al., Blood 103 (2004) 3783-3788; Lee, K. N., et al., Blood 107 (2006) 1397-1404), comprising the amino acid positions 26-760 from Swissprot database Accession number Q12884. The dimer of soluble Seprase is a 160 kDa glycoprotein consisting of two identical monomeric soluble Seprase protein units. Piñeiro-Sánchez et al. (supra) found that a increased expression of Seprase correlates with the invasive phenotype of human melanoma and carcinoma cells. Henry, L. R., et al., Clin. Cancer Res. 13 (2007) 1736-1741 describe that human colon tumor patients having high levels of stromal Seprase are more likely to have aggressive disease progression and potential development of metastases or recurrence.

Human dipeptidyl peptidase IV (=DPPIV), which is also known as CD26, is in the sense of the present disclosure a 110 kDa cell surface molecule. The amino acid sequence of human DPPIV protein comprises 766 amino acids and is shown in SEQ ID NO: 7 (Swissprot database Accession No. P27487). It contains intrinsic dipeptidyl peptidase IV activity which selectively removes N-terminal dipeptide from peptides with proline or alanine in the third amino acid position. It interacts with various extracellular molecules and is also involved in intracellular signal transduction cascades. The multifunctional activities of human DPPIV are dependent on cell type and intracellular or extracellular conditions that influence its role as a proteolytic enzyme, cell surface receptor, co-stimulatory interacting protein and signal transduction mediator. Human DPPIV has a short cytoplasmatic domain from amino acid position 1 to 6, a transmembrane region from amino acid position 7 to 28, and an extracellular domain from amino acid position 29 to 766 with intrinsic dipeptidyl peptidase IV (DPPIV) activity. Human soluble dipeptidyl peptidase IV (=soluble DPPIV) amino acid sequence comprises the amino acid positions 29 to 766 from Swissprot database Accession number P27487. The dimer of soluble DPPIV is a 170 kDa glycoprotein consisting of two identical monomeric soluble DPPIV units.

The "soluble DPPIV/Seprase protein complex" (=DPPIV/Seprase) in the sense of the present disclosure refers to the soluble complex formed of a soluble DPPIV homodimer (170 kDa) and a soluble Seprase homodimer (160 kDa) with a molecular weight of 330 kDa. Under certain conditions this complex may form a double complex having a molecular weight of 660 kDa.

As obvious to the skilled artisan, the present disclosure shall not be construed to be limited to the full-length protein ASC of SEQ ID NO:1. Physiological or artificial fragments of protein ASC, secondary modifications of protein ASC, as well as allelic variants of protein ASC are also encompassed by the present disclosure. Variants of a polypeptide are encoded by the same gene, but may differ in their isoelectric point (=PI) or molecular weight (=MW), or both e.g., as a result of alternative mRNA or pre-mRNA processing. The amino acid sequence of a variant is to 95% or more identical to the corresponding marker sequence. Artificial fragments may encompass a peptide produced synthetically or by recombinant techniques, which at least comprises one epitope of diagnostic interest consisting of at least 6, 7, 8, 9 or 10 contiguous amino acids as derived from the sequence disclosed in SEQ ID NO:1. Such fragment may advantageously be used for generation of antibodies or as a standard in an immunoassay.

The inventors of the present disclosure have now found and could establish that an increased concentration for protein ASC as determined from a body fluid sample derived from an individual is indicative for COPD.

The practicing of the present disclosure will employ, unless otherwise indicated, conventional techniques of molecular biology (including recombinant techniques), microbiology, cell biology, biochemistry, and immunology, which are within the skill of the art. Such techniques are explained fully in the literature, such as, Sambrook, et al., Molecular Cloning: A Laboratory Manual, second edition, (1989); Gait, M. J., (ed.) Oligonucleotide Synthesis (1984); Freshney, R. I., (ed.), Animal Cell Culture (1987); Methods in Enzymology (Academic Press, Inc.); Ausubel, F. M., et al., (eds.), Current Protocols in Molecular Biology (1987) and periodic updates; Mullis, et al., (eds.) PCR: The Polymerase Chain Reaction (1994).

Unless defined otherwise, technical and scientific terms used herein have the same meaning as commonly understood by one of ordinary skill in the art to which this disclosure belongs. Singleton, et al., Dictionary of Microbiology and Molecular Biology, 2nd ed., John Wiley & Sons, New York, N.Y. (1994); March, Advanced Organic Chemistry Reactions, Mechanisms and Structure, 4th ed., John Wiley & Sons, New York, N.Y. (1992); Lewin, B., Genes V, published by Oxford University Press (1994), ISBN 0-19-854287 9; Kendrew, J., et al., (eds.), The Encyclopedia of Molecular Biology, published by Blackwell Science Ltd. (1994), ISBN 0-632-02182-9; and Meyers, R. A., (ed.), Molecular Biology and Biotechnology: a Comprehensive Desk Reference, published by VCH Publishers, Inc. (1995), ISBN 1-56081-569 8) provide one skilled in the art with a general guide to many of the terms used in the present application.

As used herein, each of the following terms has the meaning associated with it in this section.

The articles "a" and "an" are used herein to refer to one or to more than one (i.e. to at least one) of the grammatical object of the article. By way of example, "a marker" means one marker or more than one marker. The term "at least" is used to indicate that optionally one or more than one further objects may be present.

The expression "one or more" denotes 1 to 50, for example 1 to 20 or also 2, 3, 4, 5, 6, 7, 8, 9, 10, 12, or 15.

The term "marker" or "biochemical marker" as used herein refers to a molecule to be used as a target for analyzing an individual's test sample. In one embodiment examples of such molecular targets are proteins or polypeptides. Proteins or polypeptides used as a marker in the present disclosure are contemplated to include naturally occurring variants of said protein as well as fragments of said protein or said variant, in particular, immunologically detectable fragments. Immunologically detectable fragments may comprise at least 6, 7, 8, 10, 12, 15 or 20 contiguous amino acids of said marker polypeptide. One of skill in the art would recognize that proteins which are released by cells or present in the extracellular matrix may be damaged, e.g., during inflammation, and could become degraded or cleaved into such fragments. Certain markers are synthesized in an inactive form, which may be subsequently activated by proteolysis. As the skilled artisan will appreciate, proteins or fragments thereof may also be present as part of a complex. Such complex also may be used as a marker in the sense of the present disclosure. In addition, or in the alternative a marker polypeptide or a variant thereof may carry a post-translational modification. Exemplary posttranslational modifications are glycosylation, acylation, or phosphorylation.

The term "label" as used herein refers to any substance that is capable of producing a signal via direct or indirect detection. For direct detection the labeling group or label suitable for use in the present disclosure can be selected from any known detectable marker groups, but are not limited to, chromogens, fluorescent, chemiluminescent groups (e.g. acridinium esters or dioxetanes), electrochemiluminescent compounds, catalysts, enzymes, enzymatic substrates, dyes, fluorescent dyes (e.g. fluorescein, coumarin, rhodamine, oxazine, resorufin, cyanine and derivatives thereof), colloidal metallic and nonmetallic particles, and organic polymer latex particles. Other examples of labeling groups are luminescent metal complexes, such as ruthenium or europium complexes, enzymes, e.g. as used for ELISA, and radioisotopes.

Indirect detection systems comprise, for example, that the detection reagent, e.g. the detection antibody, is labeled with a first partner of a bioaffine binding pair. Examples of suitable binding pairs are hapten or antigen/antibody, biotin or biotin analogues such as aminobiotin, iminobiotin or desthiobiotin/avidin or streptavidin, sugar/lectin, nucleic acid or nucleic acid analogue/complementary nucleic acid, and receptor/ligand, e.g. steroid hormone receptor/steroid hormone. Exemplary first binding pair members comprise hapten, antigen and hormone. Exemplary haptens include digoxin and biotin and analogues thereof. The second partner of such binding pair, e.g. an antibody, streptavidin, etc., usually is labeled to allow for direct detection, e.g. by the labels as mentioned above.

The term "assessing chronic obstructive pulmonary disease" or "assessing COPD" is used to indicate that the method according to the present disclosure will alone or together with other markers or variables, e.g., aid the physician to establish or confirm the absence or presence of COPD. The method will e.g. be useful to establish or confirm the absence or presence of COPD.

A "marker for COPD" in the sense of the present disclosure is a marker that, as single marker, or if combined with the marker ASC, adds relevant information in the assessment of COPD to the diagnostic question under investigation. The information is considered relevant or of additive value if at a given specificity the sensitivity, or if at a given sensitivity the specificity, respectively, for the assessment of COPD can be improved by including said marker into a marker panel (marker combination) already comprising the marker ASC. In at least some embodiments, the improvement in sensitivity or specificity, respectively, is statistically significant at a level of significance of $p=0.05$, $0.02$, $0.01$ or lower.

The term "sample" or "test sample" as used herein refers to a biological sample obtained from an individual for the purpose of evaluation in vitro. In the methods of the present disclosure, the sample or patient sample may comprise in an embodiment of the present disclosure any body fluid. Exemplary samples are body fluids, such as serum, plasma, or whole blood.

Protein ASC, particularly soluble forms of protein ASC, are determined in vitro in an appropriate sample. For example, the sample is derived from a human subject, e.g. a COPD patient or a person in risk of COPD or a person suspected of having COPD. Also, in some embodiments, protein ASC is determined in a serum or plasma sample.

The term "reference sample" as used herein refers to a biological sample provided from a reference group of apparently healthy individuals for the purpose of evaluation in vitro. The term "reference concentration" as used herein refers to a value established in a reference group of apparently healthy individuals.

It is known to a person skilled in the art that the measurement results of step (a) according to the method(s) of the present disclosure will be compared to a reference concentration. Such reference concentration can be determined using a negative reference sample, a positive reference sample, or a mixed reference sample comprising one or more than one of these types of controls. A negative reference sample may comprise a sample from non smokers, control smokers with no diagnosis of COPD, asthma or various combinations thereof, for example. In at least some embodiments, a positive reference sample comprises a sample from a subject with the diagnosis of COPD.

The expression "comparing the concentration determined to a reference concentration" is merely used to further illustrate what is obvious to the skilled artisan anyway. A reference concentration is established in a control sample. The control sample may be an internal or an external control sample. In one embodiment an internal control sample is used, i.e. the marker level(s) is(are) assessed in the test sample as well as in one or more other sample(s) taken from the same subject to determine if there are any changes in the level(s) of said marker(s). In another embodiment an external control sample is used. For an external control sample the presence or amount of a marker in a sample derived from the individual is compared to its presence or amount in an individual known to suffer from, or known to be at risk of, a given condition; or an individual known to be free of a given condition, i.e., "normal individual". For example, a marker level in a patient sample can be compared to a level known to be associated with a specific course of COPD. Usually the sample's marker level is directly or indirectly correlated with a diagnosis and the marker level is e.g. used to determine whether an individual is at risk for COPD. Alternatively, the sample's marker level can e.g. be compared to a marker level known to be associated with a response to therapy in COPD patients, the diagnosis of COPD, the guidance for selecting an appropriate drug to COPD, in judging the risk of disease progression, or in the follow-up of COPD patients. Depending on the intended diagnostic use an appropriate control sample is chosen and a control or reference value for the marker established therein. It will be appreciated by the skilled artisan that such control sample in one embodiment is obtained from a reference population that is age-matched and free of confounding diseases. As also clear to the skilled artisan, the absolute marker values established in a control sample will be dependent on the assay used. In some embodiments, samples from 100 well-characterized individuals from the appropriate reference population may be used to establish a control (reference) value. Also, the reference population may be chosen to consist of 20, 30, 50, 200, 500 or 1000 individuals. Healthy individuals represent a reference population for establishing a control value.

The term "measurement", "measuring" or "determining" comprise a qualitative, a semi-quantitative or a quantitative measurement. In the present disclosure protein ASC is measured in a body fluid sample. In an exemplary embodiment the measurement is a semi-quantitative measurement, i.e. it is determined whether the concentration of protein ASC is above or below a cut-off value. As the skilled artisan will appreciate, in a Yes—(presence) or No—(absence) assay, the assay sensitivity is usually set to match the cut-off value.

The values for protein ASC as determined in a control group or a control population are for example used to establish a cut-off value or a reference range. A value above such cut-off value or out-side the reference range at its higher end is considered as elevated or as indicative for the presence of COPD.

In an embodiment a fixed cut-off value is established. Such cut-off value is chosen to match the diagnostic question of interest.

In an embodiment, the cut-off is set to result in a specificity of 90%, or in some cases the cut-off is set to result in a specificity of 95%, or even set to result in a specificity of 98%.

In an embodiment the cut-off is set to result in a sensitivity of 90%, a sensitivity of 95%, or the cut-off is set to result in a sensitivity of 98%.

In some embodiments, values for protein ASC as determined in a control group or a control population are used to establish a reference range. In embodiments a concentration of protein ASC is considered as elevated if the value determined is above the 90%-percentile of the reference range. In further embodiments a concentration of protein ASC is considered as elevated if the value determined is above the 95%-percentile, the 96%-percentile, the 97%-percentile or the 97.5%-percentile of the reference range.

A value above the cut-off value can for example be indicative for the presence of COPD. A value below the cut-off value can for example be indicative for the absence of COPD.

In further embodiments the measurement of protein ASC is a quantitative measurement. In further embodiments the concentration of protein ASC is correlated to an underlying diagnostic question.

A sample provided from a patient with already confirmed COPD in certain settings might be used as a positive control sample and assayed in parallel with the sample to be investigated. In such setting a positive result for the marker protein ASC in the positive control sample indicates that the testing procedure has worked on the technical level.

As the skilled artisan will appreciate, any such assessment is made in vitro. The sample (test sample) is discarded afterwards. The sample is solely used for the in vitro diagnostic method of the disclosure and the material of the sample is not transferred back into the patient's body. Typically, the sample is a body fluid sample, e.g., serum, plasma, or whole blood.

The method according to the present disclosure is based on a liquid or body fluid sample which is obtained from an individual and on the in vitro determination of protein ASC in such sample. An "individual" as used herein refers to a single human or non-human organism. Thus, the methods and compositions described herein are applicable to both human and veterinary disease. In at least some embodiments, the individual, subject, or patient is a human being.

According to some embodiments, the marker protein ASC is specifically determined in vitro from a liquid sample by use of a specific binding agent. In some embodiments according to the present disclosure, the concentration of protein ASC is determined. In an embodiment, the concentration of marker protein ASC is specifically determined in vitro from a sample by use of a specific binding agent.

A specific binding agent is, e.g., a receptor for the protein ASC, a lectin binding to protein ASC, an antibody to protein ASC, peptidebodies to protein ASC, bispecific dual binders or bispecific antibody formats. A specific binding agent has at least an affinity of $10^7$ l/mol for its corresponding target molecule. The specific binding agent may have an affinity of $10^8$ l/mol or also of $10^9$ l/mol for its target molecule.

As the skilled artisan will appreciate the term specific is used to indicate that other biomolecules present in the sample do not significantly bind to the binding agent specific for the protein ASC sequence of SEQ ID NO:1. In some embodiments, the level of binding to a biomolecule other than the target molecule results in a binding affinity which is at most only 10% or less, only 5% or less only 2% or less or only 1% or less of the affinity to the target molecule, respectively. Specific binding agent may fulfill both the above minimum criteria for affinity as well as for specificity.

Examples of specific binding agents are peptides, peptide mimetics, aptamers, spiegelmers, darpins, ankyrin repeat proteins, Kunitz type domains, antibodies, single domain antibodies, (see: Hey, T., et al., Trends Biotechnol. 23 (2005) 514-522) and monovalent fragments of antibodies. In certain embodiments the specific binding agent is a polypeptide. In certain embodiments the specific binding agent is an antibody or a monovalent antibody fragment, for example a monovalent fragment derived from a monoclonal antibody. Monovalent antibody fragments include, but are not limited to Fab, Fab'-SH, single domain antibody, Fv, and scFv fragments, as provided below.

The term "antibody" herein is used in the broadest sense and specifically covers monoclonal antibodies, polyclonal antibodies, multispecific antibodies (e.g. bispecific antibodies) formed from at least two intact antibodies, and antibody fragments so long as they exhibit the desired biological activity. In certain embodiments the specific binding agent is an antibody or a monovalent antibody fragment, for example a monovalent fragment derived from a monoclonal antibody.

An "isolated" antibody is one which has been identified and separated and/or recovered from a component of its natural environment. Contaminant components of its natural environment are materials which would interfere with research, diagnostic or therapeutic uses for the antibody, and may include enzymes, hormones, and other proteinaceous or non-proteinaceous solutes. In some embodiments, an antibody is purified (1) to greater than 95% by weight of antibody as determined by, for example, the Lowry method, and in some embodiments, to greater than 99% by weight; (2) to a degree sufficient to obtain at least 15 residues of N-terminal or internal amino acid sequence by use of, for example, a spinning cup sequenator, or (3) to homogeneity by SDS-PAGE under reducing or nonreducing conditions using, for example, Coomassie blue or silver stain. Isolated antibody includes the antibody in situ within recombinant cells since at least one component of the antibody's natural environment will not be present. Ordinarily, however, isolated antibody will be prepared by at least one purification step.

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end; the constant domain of the light chain is aligned with the first constant domain of the heavy chain, and the light-chain variable domain is aligned with the variable domain of the heavy chain. Particular amino acid residues are believed to form an interface between the light-chain and heavy-chain variable domains.

The "variable region" or "variable domain" of an antibody refers to the amino-terminal domains of the heavy or light chain of the antibody. The variable domain of the heavy chain may be referred to as "VH." The variable domain of the light chain may be referred to as "VL." These domains are generally the most variable parts of an antibody and contain the antigen-binding sites.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions (HVRs) both in the light-chain and the heavy-chain variable domains. The more highly conserved portions of variable domains are called the framework regions (FR). The variable domains of native heavy and light chains each comprise four FR regions, largely adopting a beta-sheet configuration, connected by three HVRs, which form loops connecting, and in some cases forming part of, the beta-sheet structure. The HVRs in each chain are held together in close proximity by the FR regions and, with the HVRs from the other chain, contribute to the formation of the antigen-binding site of antibodies (see Kabat, et al., Sequences of Proteins of Immunological Interest, 5th ed., National Institute of Health, Bethesda, Md. (1991)). The constant domains are not involved directly in the binding of an antibody to an antigen, but exhibit various effector functions, such as participation of the antibody in antibody-dependent cellular toxicity.

The "light chains" of antibodies (immunoglobulins) from any vertebrate species can be assigned to one of two clearly distinct types, called kappa (κ) and lambda (λ), based on the amino acid sequences of their constant domains.

Depending on the amino acid sequences of the constant domains of their heavy chains, antibodies (immunoglobulins) can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1, and IgA2. The subunit structures and three-dimensional configurations of different classes of immunoglobulins are well known and described generally in, for example, Abbas, et al., Cellular and Mol. Immunology, 4th ed., W.B. Saunders, Co. (2000). An antibody may be part of a larger fusion molecule, formed by covalent or non-covalent association of the antibody with one or more other proteins or peptides.

The terms "full-length antibody," "intact antibody," and "whole antibody" are used herein interchangeably to refer to an antibody in its substantially intact form, not antibody fragments as defined below. The terms particularly refer to an antibody with heavy chains that contain an Fc region.

"Antibody fragments" comprise a portion of an intact antibody, for example comprising the antigen-binding region thereof. Examples of antibody fragments include Fab, Fab', F(ab')2, and Fv fragments; diabodies; linear antibodies; single-chain antibody molecules; and multispecific antibodies formed from antibody fragments.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields a F(ab')2 fragment that has two antigen-combining sites and is still capable of cross-linking antigen.

"Fv" is the minimum antibody fragment which contains a complete antigen-binding site. In one embodiment, a two-chain Fv species consists of a dimer of one heavy- and one light-chain variable domain in tight, non-covalent association. In a single-chain Fv (scFv) species, one heavy- and one light-chain variable domain can be covalently linked by a flexible peptide linker such that the light and heavy chains can associate in a "dimeric" structure analogous to that in a two-chain Fv species. It is in this configuration that the three HVRs of each variable domain interact to define an antigen-binding site on the surface of the VH-VL dimer. Collectively, the six HVRs confer antigen-binding specificity to the antibody. However, even a single variable domain (or half of an Fv comprising only three HVRs specific for an antigen) has the ability to recognize and bind antigen, although at a lower affinity than the entire binding site.

The Fab fragment contains the heavy- and light-chain variable domains and also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody-hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them. Other chemical couplings of antibody fragments are also known.

"Single-chain Fv" or "scFv" antibody fragments comprise the VH and VL domains of an antibody, wherein these domains are present in a single polypeptide chain. Generally, the scFv polypeptide further comprises a polypeptide linker between the VH and VL domains that enables the scFv to form the desired structure for antigen binding. For a review of scFv, see, e.g., Pluckthuen, A., In: The Pharmacology of Monoclonal Antibodies, vol. 113, Rosenburg and Moore (eds.), Springer-Verlag, New York (1994) pp. 269-315.

The term "diabodies" refers to antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies may be bivalent or bispecific. Diabodies are described more fully in, for example, EP 0404 097; WO 1993/01161; Hudson, et al., Nat. Med. 9 (2003) 129-134; and Hollinger, et al., PNAS USA 90 (1993) 6444-6448. Triabodies and tetrabodies are also described in Hudson, et al., Nat. Med. 9 (2003) 129-134.

The term "monoclonal antibody" as used herein refers to an antibody obtained from a population of substantially homogeneous antibodies, i.e., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. In certain embodiments, such a monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. It should be understood that a selected target binding sequence can be further altered, for example, to improve affinity for the target, to humanize the target-binding sequence, to improve its production in cell culture, to reduce its immunogenicity in vivo, to create a multispecific antibody, etc., and that an antibody comprising the altered target binding sequence is also a monoclonal antibody of this disclosure. In contrast to polyclonal antibody preparations, which typically include different antibodies directed against different determinants (epitopes), each monoclonal antibody of a monoclonal-antibody preparation is directed against a single determinant on an antigen. In addition to their specificity, monoclonal-antibody preparations are advantageous in that they are typically uncontaminated by other immunoglobulins.

A specific binding agent may comprise an antibody reactive with SEQ ID NO: 1.

For the achievements as disclosed in the present disclosure antibodies from various sources may be used. Standard protocols for obtaining antibodies can be as well used as modern alternative methods. Alternative methods for generation of antibodies comprise amongst others the use of synthetic or recombinant peptides, representing a clinically relevant epitope of ASC for immunization. Alternatively, DNA immunization also known as DNA vaccination may be used. Clearly monoclonal antibodies or polyclonal antibodies from different species, e.g., rabbits, sheep, goats, rats or guinea pigs can be used. Since monoclonal antibodies can be produced in any amount required with constant properties, they represent useful tools in development of an assay for clinical routine.

As the skilled artisan will appreciate now, that protein ASC has been identified as a marker which is useful in the assessment of COPD. Various immunodiagnostic procedures may be used to reach data comparable to the achievements of the present disclosure.

For determination of protein ASC the sample obtained from an individual is incubated in vitro with the specific binding agent for ASC under conditions appropriate for formation of a binding agent ASC complex. Such conditions need not be specified, since the skilled artisan without any inventive effort can easily identify such appropriate incubation conditions. The amount of binding agent ASC complex is determined and used in the assessment of COPD. As the skilled artisan will appreciate there are numerous methods to determine the amount of the specific binding agent ASC complex all described in detail in relevant textbooks (cf., e.g., Tijssen, P., supra, or Diamandis, E. P., and Christopoulos, T. K. (eds.), Immunoassay, Academic Press, Boston (1996)).

Immunoassays are well known to the skilled artisan. Methods for carrying out such assays as well as practical applications and procedures are summarized in related textbooks. Examples of related textbooks are Tijssen, P., Preparation of enzyme-antibody or other enzyme-macromolecule conjugates, In: Practice and theory of enzyme immunoassays, pp. 221-278, Burdon, R. H. and v. Knippenberg, P. H. (eds.), Elsevier, Amsterdam (1990), and various volumes of Colowick, S. P., and Caplan, N. O., (eds.), Methods in Enzymology, Academic Press, dealing with immunological detection methods, especially volumes 70, 73, 74, 84, 92 and 121.

The present disclosure also relates in an embodiment to the use of an antibody specifically binding to protein ASC in a method according to the present disclosure. In one embodiment in a method according to the present disclosure protein ASC is measured in an immunoassay procedure. In a further embodiment protein ASC is detected in an enzyme-linked immunoassay (ELISA).

In a further embodiment protein ASC is detected in a sandwich assay (sandwich-type assay format). In such assay, a first specific binding agent is used to capture protein ASC on the one side and a second specific binding agent, which is labelled to be directly or indirectly detectable, is used on the other side. The specific binding agents used in a sandwich-type assay format may be antibodies specifically directed against protein ASC. On the one hand, the detection may be carried out by using different capturing and labelled antibodies, i.e. antibodies which recognize different epitopes on the ASC polypeptide. On the other hand, a sandwich-type assay may also be carried out with a capture and labelling antibody which is directed against the same epitope of protein ASC. In this embodiment, only di- and multimeric forms of protein ASC may be detected. In an embodiment an antibody to protein ASC is used in a qualitative (ASC present or absent) or quantitative (amount of ASC is determined) immunoassay.

In a further embodiment the method according to the present disclosure is based on the measurement of ASC, wherein said measurement of ASC is performed in a sandwich immunoassay employing at least two antibodies reactive with at least two non-overlapping epitopes.

In a further embodiment protein ASC is detected in a competitive assay. In such assay format a binding agent specifically binding to ASC of SEQ ID NO: 1 is used. In a mixture labeled ASC that has been added to the mixture and ASC comprised in a sample compete for binding to the specific binding agent. The extent of such competition can be measured according to standard procedures.

The concentration of the protein ASC in test samples may be determined in vitro using a specific ELISA, as already described above. Using this assay format, the inventors have shown that samples from patients already diagnosed as having COPD by classical methods, e.g. spirometry, can be distinguished from samples from apparently healthy individuals. Results are shown in the example section of this application.

The inventors of the present disclosure surprisingly are able to detect protein ASC in a body fluid sample. Even more surprising they are able to demonstrate that the presence of protein ASC in such liquid sample obtained from an individual can be correlated to COPD. No tissue and no biopsy sample is required to make use of the marker ASC in the assessment of COPD. Measuring the level of protein ASC in (e.g. a small aliquot of) a simple body fluid sample is considered very advantageous in the field of COPD.

In an exemplary embodiment the method according to the present disclosure is practiced with serum as sample material. In some embodiments the method according to the present disclosure is practiced with plasma as sample material. In further embodiments the method according to the present disclosure is practiced with whole blood as sample material.

In further embodiments, the present disclosure relates to use of protein ASC as a marker molecule in the in vitro assessment of COPD from a liquid sample obtained from an individual.

In some situation, a single event or process may cause the respective disease as, e.g., in infectious diseases. In other cases, especially when the etiology of the disease is not fully understood as is the case for COPD, correct diagnosis can be very difficult. As the skilled artisan will appreciate, no biochemical marker is diagnostic with 100% specificity and at the same time 100% sensitivity for a given multifactorial disease, as for example for COPD. Rather, biochemical markers are used to assess with a certain likelihood or predictive value an underlying diagnostic question, e.g., the presence, absence, or the severity of a disease. Therefore in routine clinical diagnosis, generally various clinical symptoms and biological markers are considered together in the assessment of an underlying disease. The skilled artisan is fully familiar with the mathematical/statistical methods that routinely are used to calculate a relative risk or likelihood for the diagnostic question to be assessed. In routine clinical practice various clinical symptoms and biological markers are generally considered together by a physician in the diagnosis, treatment, and management of the underlying disease.

COPD patients are traditionally treated with bronchodilators or steroids and examined by spirometry for reversibility of airflow obstruction. If reversibility is less than 15%, and particularly if they have a long history of smoking, then they would be classified as COPD patients.

The ATS (American Thoracic Society) criteria for diagnosing COPD are as follows:
FEV1/FVC ratio<0.7
FEV1<70% predicted, <15% reversibility to inhaled B2 agonist:
2 week oral prednisolone trial-less than 15% reversibility in FEV1
Smoking history FEV1 is the volume of air expelled from the lungs in one second, starting from a position of maximum inspiration and with the subject making maximum effort. FEV1% is the FEV1 expressed as a percentage of the forced vital capacity (FVC). The FVC is the total volume of air expelled from the lungs from a position of maximum inspiration with the subject making maximum effort. FEV1 may be measured using a spirometer to measure the volume of air expired in the first second of exhalation.

The spirometric classification of COPD according to the ATS (American Thoracic Society)/European respiratory Society 2004 is shown in Table 1. ATS COPD Stage 0 is currently no longer used in the ATS classification system.

TABLE 1

| COPD Stage | Severity | Postbronchdilator FEV1/FVC | FEV1% pred |
|---|---|---|---|
| 0 | At risk[#] | >0.7 | ≥80% |
| I | Mild COPD | ≤0.7 | ≥80% |
| II | Moderate COPD | ≤0.7 | 50%-80% |
| III | Severe COPD | ≤0.7 | 30%-50% |
| IV | Very severe COPD | ≤0.7 | <30% |

FEV1: forced expiratory volume in one second;
FVC: forced vital capacity;
[#]patients who smoke or have exposure to pollutants, have cough, sputum or dyspnoea, have family history of respiratory disease.

In the assessment of COPD the marker protein ASC will be of advantage in one or more of the following aspects: assessment; screening; staging of disease; monitoring of disease progression; prognosis; guidance of therapy and monitoring of the response to therapy. Exemplary areas of diagnostic relevance in assessing an individual suspected or known to have COPD are screening, staging of disease, monitoring of disease progression and monitoring of the response to therapy.

Screening (assessment whether individuals are at risk for developing COPD or have COPD): is defined as the systematic application of a test to identify individuals e.g. at risk individuals, for indicators of a disease, e.g., the presence of COPD. For example, the screening population may be composed of individuals known to be at higher than average risk of COPD. For example, a screening population for COPD is composed of individuals known to be at higher than average risk of COPD, like smokers and ex-smokers.

Screening in the sense of the present disclosure relates to the unbiased assessment of individuals regarding their risk for developing COPD. In an embodiment the method according to the present disclosure is used for screening purposes. I.e., it is used to assess subjects without a prior diagnosis of COPD by a) determining the concentration of protein ASC in a sample in vitro, and b) comparing the concentration of protein ASC determined in step (a) with a reference concentration of protein ASC, wherein a concentration of protein ASC above the reference concentration is indicative for the presence of COPD. In an embodiment, a body fluid sample such as blood, serum, or plasma is used as a sample in the screening for COPD.

Measurement of protein ASC will aid the physician to assess the presence or absence of COPD in an individual suspected to have COPD.

In an embodiment the present disclosure relates to an in vitro method for assessing the presence or absence of chronic obstructive pulmonary disease (COPD) in a subject, comprising a) determining the concentration of protein ASC in a sample, and b) comparing the concentration of protein ASC determined in step (a) with a reference concentration of protein ASC, wherein a concentration of protein ASC above the reference concentration is indicative for the presence of COPD. In some embodiments the sample is a body fluid sample. In further embodiments, the sample is selected from the group consisting of serum, plasma and whole blood.

In an embodiment the present disclosure relates to an in vitro method for assessing the presence or absence of chronic obstructive pulmonary disease (COPD) in a subject, comprising a) determining the concentration of protein ASC in a sample, b) comparing the concentration of protein ASC determined in step (a) with a reference concentration of protein ASC, and c) assessing the presence or absence of COPD based on the comparison of step (b), wherein a concentration of protein ASC above the reference concentration is indicative for the presence of COPD. In an exemplary embodiment the sample is a body fluid sample. In further embodiments, the sample is selected from the group consisting of serum, plasma and whole blood.

In some embodiments, the present disclosure relates to an in vitro method of assessing for a subject the presence or absence of COPD, the method comprising a) determining the concentration of protein ASC in a sample, and b) comparing the concentration of protein ASC determined in step (a) with a cut-off value for protein ASC established in a reference population, wherein a concentration of protein ASC above the cut-off value is indicative for the presence of COPD. In an embodiment the present disclosure relates to an in vitro method of assessing for a subject the presence or absence of COPD, the method comprising a) determining the concentration of protein ASC in a sample, and b) comparing the concentration of protein ASC determined in step (a) with a cut-off value for protein ASC established in a reference population, wherein a concentration of protein ASC below the cut-off value is indicative for the absence of COPD.

In an embodiment the present disclosure relates to the use of the protein ASC in the assessment of COPD. For example, protein ASC may used in the assessment of the presence or absence of COPD.

In a further embodiment the present disclosure relates to the use of the protein ASC in the in vitro assessment of COPD in a sample, wherein a concentration of protein ASC above a reference concentration for protein ASC is indicative for COPD.

In some embodiments the sample according the use is a body fluid sample. For example, in some embodiments said body fluid sample according the use is selected from the group consisting of serum, plasma and whole blood.

In a further embodiment the present disclosure relates to the use of the protein ASC in the in vitro assessment of COPD in a body fluid sample, wherein a concentration of protein ASC above a reference concentration for protein ASC in a body fluid sample is indicative for the presence of COPD.

In a further embodiment the present disclosure relates to the use of the protein ASC in the in vitro assessment of COPD in a serum, plasma, or whole blood sample, wherein a concentration of protein ASC above a reference concentration for protein ASC in a serum, plasma, or whole blood sample is indicative for the presence of COPD.

One embodiment of the present disclosure refers to the screening of a population to distinguish between individuals which are probably free from COPD and individuals which probably have COPD. The latter group of individuals may then be subject to further diagnostic procedures, e.g. by lung function testing, spirometry or other suitable means.

In an embodiment the in vitro method according to the present disclosure is characterized in that the assessment of the protein ASC takes place for classifying a patient according to be at risk to have COPD for clinical decisions, particularly further treatment by means of medications for the treatment or therapy of COPD, and for treatment or therapy of infection/inflammatory diseases of the airway and lung, as well as for therapy control of an antibiotic treatment or therapeutic antibody treatment.

In an embodiment the present disclosure relates to an in vitro method for assessing whether an individual is at risk for developing COPD comprising the steps of a) determining the concentration of protein ASC in a sample, and b) of assessing said individual's risk for developing COPD by comparing the concentration of protein ASC determined in step (a) with a reference concentration of protein ASC, wherein a concentration of protein ASC above a reference concentration is indicative for an individual to be at risk for developing COPD.

In an embodiment the present disclosure relates to an in vitro method for assessing whether an individual is at risk for developing COPD comprising the steps of a) determining the concentration of protein ASC in a body fluid sample, and b) of assessing said individual's risk for developing COPD by comparing the concentration of protein ASC determined in step (a) with a reference concentration of protein ASC, wherein a concentration of protein ASC above a reference concentration is indicative for an individual to be at risk for developing COPD. In an exemplary embodiment the body fluid sample is selected from the group consisting of serum, plasma and whole blood.

Staging of Patients.

Surprisingly the inventors have found that the use of the protein ASC can lead to an in vitro classification of a COPD patient to a COPD stage of the disease, e.g. into a COPD stage from 0-IV according to the ATS classification, respectively.

In an embodiment the present disclosure relates to an in vitro method aiding in the staging of COPD patients, comprising the steps of a) determining the concentration of protein ASC in a sample, b) comparing the concentration of protein ASC determined in step (a) with a reference concentration of protein ASC, and staging COPD by comparing the concentration determined in step (a) to the concentration of this marker previously established as indicative for the stage of COPD.

In an embodiment the present disclosure relates to an in vitro method aiding in the staging of COPD patients, comprising the steps of a) determining the concentration of protein ASC in a body fluid sample, b) comparing the concentration of protein ASC determined in step (a) with a reference concentration of protein ASC, and staging COPD by comparing the concentration determined in step (a) to the concentration of this marker to its reference value(s) indicative of a certain stage of COPD. In some embodiments the body fluid sample is selected from the group consisting of serum, plasma and whole blood. For example, the concentration of ASC may be used as an aid in classifying the individuals investigated into the group of individuals that are clinically "normal", into the group of patients at risk of having COPD, and the group of patients having COPD. In certain embodiments the concentration of ASC may further be used to group patients as stage 0-IV, respectively according to the ATS classification system (American Thoracic Society/European respiratory Society 2004 classification shown in table 1). The skilled artisan is aware of other available COPD classification systems. In an embodiment a protein selected from the group consisting of APEX1, ASC, NNMT and Seprase is used to classify a COPD patient to a COPD stage. In a further embodiment of the present disclosure the protein ASC may be used in the in vitro classification of a COPD patient to a COPD stage. Experimental results for the use of protein ASC to classify a COPD patient to a COPD stage are shown in Example 4, FIGS. 3 and 4.

Prognosis.

Prognostic indicators can be defined as clinical, pathological or biochemical features of COPD patients that predict with a certain likelihood the disease outcome. Their main use is to help to rationally plan patient management, i.e. to avoid undertreatment of aggressive disease and overtreatment of indolent disease, respectively.

As the level of protein ASC alone significantly contributes to the differentiation of COPD patients from healthy controls or other diseases of the lung (e.g. asthma, bronchitis, pulmonary fibrosis and tuberculosis), it has to be expected that it will aid in assessing the prognosis of patients suffering from COPD. The concentration of protein ASC may be combined with results of lung function testing or spirometry.

Differentiation of COPD from Asthma.

In a further embodiment the method according to the present disclosure is used to differentiate COPD from other types of lung diseases, for example asthma.

According to the instant disclosure, the protein ASC may also be used to differentiate COPD from other types of lung diseases, e.g. asthma, bronchitis, pulmonary fibrosis and tuberculosis. Surprisingly the inventors have found that the use of a marker combination of a COPD specific marker, for example ASC, and an inflammation marker selected from the group consisting of CRP, interleukin-6, serum amyloid A, S100 and E-selectin, can lead to a differentiation between COPD and other inflammatory diseases of the lung, e.g. asthma, acute or chronic inflammation of the lung, respectively. Experimental results for the protein ASC and protein CRP are shown in the example section.

Monitoring of Disease Progression.

At present it is very difficult to predict with a reasonable likelihood whether a patient diagnosed with COPD has a more or less stable status or whether the disease will progress.

Progression of disease, i.e. of COPD, may be evaluated by in vitro monitoring of the concentration of protein ASC in test samples, especially by taking one or more consecutive samples. In an embodiment the present disclosure relates to an in vitro method for monitoring the disease progression in a patient suffering from COPD, the method comprising the steps of a) determining the concentration of protein ASC in a sample, b) comparing the concentration of protein ASC determined in step (a) with a reference concentration of protein ASC, and monitoring the disease progression by comparing the concentration determined in step (a) to the concentration of this marker as determined in a sample taken from the same patient at a previous point in time. As will be appreciated that an increase in the level of C-terminal proSP-B over time is indicative of disease progression.

Monitor a Patient's Response to Therapy.

The method according to the present disclosure, when used in patient monitoring, may be used in the follow-up of patients and e.g. help to assess efficacy of a treatment of COPD.

In an embodiment the present disclosure relates to an in vitro method for monitoring a patient's response to a treatment targeted at reducing COPD, comprising the steps of a) determining the concentration of protein ASC in a body fluid sample, b) comparing the concentration of protein ASC determined in step (a) with a reference concentration of protein ASC, and of monitoring a patient's response to COPD therapy by comparing the concentration determined in step (a) to the concentration of this marker to its reference value. In an exemplary embodiment, the body fluid sample is selected from the group consisting of serum, plasma and whole blood.

Monitoring a patient's response to therapy can be practiced e.g. by establishing the pre- and post-therapeutic marker level for protein ASC and by comparing the pre- and the post-therapeutic marker level.

A patient's response to a COPD treatment may be evaluated in vitro by monitoring the concentration of protein ASC in test samples over time. In an embodiment the present disclosure relates to an in vitro method for monitoring a patient's response to a COPD treatment, comprising the steps of a) determining the concentration of protein ASC in a sample, b) comparing the concentration of protein ASC determined in step (a) with a concentration of protein ASC established in a previous sample, wherein a decrease in protein ASC is indicative of a positive response to said treatment.

The level of protein ASC appears to be appropriate to monitor a patient's response to therapy. The present disclosure thus also relates to the use of protein ASC in monitoring a patient's response to therapy, wherein a decreased level of protein ASC is a positive indicator for an effective treatment of COPD.

Marker Combinations.

The present disclosure therefore relates in an embodiment to the use of protein ASC as one marker of a marker panel for the assessment of COPD. Such marker panel comprises protein ASC and one or more additional marker for COPD. Certain combinations of markers will e.g. be advantageous in the screening for COPD.

As the skilled artisan will appreciate there are many ways to use the measurements of two or more markers in order to improve the diagnostic question under investigation.

Biochemical markers can either be determined individually or in an embodiment of the disclosure they can be determined simultaneously, e.g. using a chip or a bead based array technology. The concentrations of the biomarkers are then either interpreted independently, e.g., using an individual cut-off for each marker, or they are combined for interpretation.

As the skilled artisan will appreciate the step of correlating a marker level to a certain likelihood or risk can be performed and achieved in different ways. For example, the determined concentration of protein ASC and the one or more other marker(s) may be mathematically combined and the combined value may correlated to the underlying diagnostic question. Marker values may be combined with the determination of ASC by any appropriate state of the art mathematical method.

In at least some embodiments, the mathematical algorithm applied in the combination of markers may be a logistic function. The result of applying such mathematical algorithm or such logistical function may be a single value. Dependent on the underlying diagnostic question such value can easily be correlated to e.g., the risk of an individual for COPD or to other intended diagnostic uses helpful in the assessment of patients with COPD. In an exemplary way, such logistic function is obtained by a) classification of individuals into the groups, e.g., into normals, individuals at risk for COPD, patients with acute or chronic inflammation of the lung and so on, b) identification of markers which differ significantly between these groups by univariate analysis, c) logistic regression analysis to assess the independent discriminative values of markers useful in assessing these different groups and d) construction of the logistic function to combine the independent discriminative values. In this type of analysis the markers are no longer independent but represent a marker combination.

In an embodiment the logistic function used for combining the values for ASC and the value of at least one further marker is obtained by a) classification of individuals into the groups of normals and individuals likely to have COPD, respectively, b) establishing the values for ASC and the value of the at least one further marker c) performing logistic regression analysis and d) construction of the logistic function to combine the marker values for ASC and the value of the at least one further marker.

A logistic function for correlating a marker combination to a disease may employ an algorithm developed and obtained by applying statistical methods. Appropriate statistical methods e.g. are Discriminant analysis (DA) (i.e., linear-, quadratic-, regularized-DA), Kernel Methods (i.e., SVM), Nonparametric Methods (i.e., k-Nearest-Neighbor Classifiers), PLS (Partial Least Squares), Tree-Based Methods (i.e., Logic Regression, CART, Random Forest Methods, Boosting/Bagging Methods), Generalized Linear Models (i.e., Logistic Regression), Principal Components based Methods (i.e., SIMCA), Generalized Additive Models, Fuzzy Logic based Methods, Neural Networks and Genetic Algorithms based Methods. The skilled artisan will have no problem in selecting an appropriate statistical method to evaluate a marker combination of the present disclosure and thereby to obtain an appropriate mathematical algorithm. In an embodiment the statistical method employed to obtain the mathematical algorithm used in the assessment of COPD is selected from DA (i.e., Linear-, Quadratic-, Regularized Discriminant Analysis), Kernel Methods (i.e., SVM), Nonparametric Methods (i.e., k-Nearest-Neighbor Classifiers), PLS (Partial Least Squares), Tree-Based Methods (i.e., Logic Regression, CART, Random Forest Methods, Boosting Methods), or Generalized Linear Models (i.e., Logistic Regression). Details relating to these statistical methods are found in the following references: Ruczinski, I., et al., J. of Computational and Graphical Statistics 12 (2003) 475-511; Friedman, J. H., J. of the American Statistical Association 84 (1989) 165-175; Hastie, T., et al., The Elements of Statistical Learning, Springer Verlag (2001); Breiman, L., et al., Classification and regression trees, Wadsworth International Group, California (1984); Breiman, L., Machine Learning 45 (2001) 5-32; Pepe, M. S., The Statistical Evaluation of Medical Tests for Classification and Prediction, Oxford Statistical Science Series, 28, Oxford University Press (2003); and Duda, R. O., et al., Pattern Classification, John Wiley & Sons, Inc., 2nd ed. (2001).

It is an embodiment of the disclosure to use an optimized multivariate cut-off for the underlying combination of biological markers and to discriminate state A from state B, e.g., normals and individuals at risk for COPD, COPD patients responsive to therapy and therapy failures, patients having an acute inflammation of the lung and COPD patients, COPD patients showing disease progression and COPD patients not showing disease progression, respectively.

The area under the receiver operator curve (=AUC) is an indicator of the performance or accuracy of a diagnostic procedure. Accuracy of a diagnostic method is best described by its receiver-operating characteristics (ROC) (see especially Zweig, M. N., and Campbell, G., Clin. Chem. 39 (1993) 561-577). The ROC graph is a plot of all of the sensitivity/specificity pairs resulting from continuously varying the decision thresh-hold over the entire range of data observed.

The clinical performance of a laboratory test depends on its diagnostic accuracy, or the ability to correctly classify subjects into clinically relevant subgroups. Diagnostic accuracy measures the test's ability to correctly distinguish two different conditions of the subjects investigated. Such conditions are for example, health and disease or disease progression versus no disease progression.

In each case, the ROC plot depicts the overlap between the two distributions by plotting the sensitivity versus 1—specificity for the complete range of decision thresholds. On the y-axis is sensitivity, or the true-positive fraction [defined as (number of true-positive test results)/(number of true-positive+number of false-negative test results)]. This has also been referred to as positivity in the presence of a disease or condition. It is calculated solely from the affected subgroup. On the x-axis is the false-positive fraction, or 1—specificity [defined as (number of false-positive results)/(number of true-negative+number of false-positive results)]. It is an index of specificity and is calculated entirely from the unaffected subgroup. Because the true- and false-positive fractions are calculated entirely separately, by using the test results from two different subgroups, the ROC plot is independent of the prevalence of disease in the sample. Each point on the ROC plot represents a sensitivity/1-specificity pair corresponding to a particular decision threshold. A test with perfect discrimination (no overlap in the two distributions of results) has an ROC plot that passes through the upper left corner, where the true-positive fraction is 1.0, or 100% (perfect sensitivity), and the false-positive fraction is 0 (perfect specificity). The theoretical plot for a test with no discrimination (identical distributions of results for the two groups) is a 45° diagonal line from the lower left corner to the upper right corner. Most plots fall in between these two extremes. (If the ROC plot falls completely below the 45° diagonal, this is easily remedied by reversing the criterion for "positivity" from "greater than" to "less than" or vice versa.) Qualitatively, the closer the plot is to the upper left corner, the higher the overall accuracy of the test.

One convenient goal to quantify the diagnostic accuracy of a laboratory test is to express its performance by a single number. The most common global measure is the area under the ROC plot (AUC). By convention, this area is always $\geq 0.5$ (if it is not, one can reverse the decision rule to make it so). Values range between 1.0 (perfect separation of the test values of the two groups) and 0.5 (no apparent distributional difference between the two groups of test values). The area does not depend only on a particular portion of the plot such as the point closest to the diagonal or the sensitivity at 90% specificity, but on the entire plot. This is a quantitative, descriptive expression of how close the ROC plot is to the perfect one (area=1.0).

The overall assay sensitivity will depend on the specificity required for practicing the method disclosed here. In certain settings a specificity of 75% may be sufficient and statistical methods and resulting algorithms can be based on this specificity requirement. In an exemplary embodiment the method used to assess individuals at risk for COPD is based on a specificity of 80%, of 85%, or even of 90% or of 95%.

Certain combinations of markers will be advantageous in the screening for COPD. In one embodiment the present disclosure is directed to an in vitro method for assessing COPD by biochemical markers, comprising determining in a sample the concentration of protein ASC and of one or more other marker(s), mathematically combining the determined concentration of protein ASC and the concentration of the one or more other marker, respectively, wherein a increased combined value is indicative for the presence of COPD.

In an embodiment the present disclosure is directed to an in vitro method for assessing COPD by biochemical markers, comprising determining in a sample the concentration of protein ASC and of one or more other marker(s) and comparing the determined concentration of protein ASC with a reference concentration of protein ASC, wherein a concentration of protein ASC above a reference concentration is indicative for the presence of COPD. In at least some embodiments, the one or more other marker of said method may be selected from the group consisting of ARMET, NNMT, FEN1, APEX1 and Seprase. In further embodiments said marker panel comprises at least protein ASC and protein APEX1. In a further embodiment said marker panel comprises at least protein ASC and protein NNMT. In a further embodiment said marker panel comprises at least protein ASC and protein FEN1. In a further embodiment said marker panel comprises at least protein ASC and protein ARMET. In an even further embodiment said marker panel comprises at least protein ASC and protein Seprase.

In some embodiments of the present disclosure, the use of marker ASC as a marker molecule for the in vitro assessment of COPD in combination with one or more marker molecule(s) indicative for COPD is disclosed. The present disclosure therefore relates, in some embodiments, to the use of protein ASC as one marker of a COPD marker panel, i.e. a marker panel comprising protein ASC and one or more additional marker for COPD screening purposes.

For example the present disclosure also relates to the use of a marker panel comprising protein ASC and ARMET, or of a marker panel comprising protein ASC and NNMT, or of a marker panel comprising protein ASC and FEN1, or of a marker panel comprising protein ASC and APEX1, or of a marker panel comprising protein ASC and Seprase, or of a marker panel comprising protein ASC and two or more markers selected from the group consisting of ARMET, NNMT, FEN1, APEX1 and Seprase.

In an embodiment markers for use in a combination with protein ASC in the method according to the present disclosure are selected from the group consisting of ARMET, NNMT, FEN1, APEX1 and Seprase. These markers may be used individually each or in any combination together with ASC for assessing COPD. In an further embodiment the present disclosure relates to a marker panel (marker combination) selected from the group consisting of protein ASC, ARMET, NNMT, FEN1, APEX1, Seprase and CRP.

In an embodiment the marker panel used in the in vitro method for assessing COPD by biochemical markers comprises the steps of determining in a sample the concentration of protein ASC and of protein NNMT, wherein a concentration of protein ASC above a reference concentration for protein ASC is indicative for the presence of COPD. In a further embodiment the marker panel used in the in vitro method comprises the marker proteins ASC, NNMT and Seprase. In a further embodiment the marker panel used in the in vitro method comprises the marker proteins ASC, NNMT, Seprase and ARMET.

In a further embodiment a marker for use in combination with protein ASC is a marker which is useful for the assessment of an inflammation (i.e. an underlying systemic inflammation).

Marker of Inflammation.

Many serum markers for the diagnosis of an inflammation are presently known. The skilled artisan is familiar with the term "marker of inflammation". Said marker of inflammation is for example selected from the interleukin-6, C-reactive protein, serum amyloid A, sE-selectin and a S100 protein.

Interleukin-6 (IL-6) is a 21 kDa secreted protein that has numerous biological activities that can be divided into those involved in hematopoiesis and into those involved in the activation of the innate immune response. IL-6 is an acute-phase reactant and stimulates the synthesis of a variety of proteins, including adhesion molecules. Its major function is to mediate the acute phase production of hepatic proteins, and its synthesis is induced by the cytokines IL-1 and TNF-. IL-6 is normally produced by macrophages and T lymphocytes. The normal serum concentration of IL-6 is <5 pg/ml.

C-reactive protein (CRP) is a homopentameric $Ca^{2+}$-binding acute phase protein with 21 kDa subunits that is involved in host defense. CRP synthesis is induced by IL-6, and indirectly by IL-1, since IL-1 can trigger the synthesis of IL-6 by Kupffer cells in the hepatic sinusoids. The normal plasma concentration of CRP is <3 µg/ml (30 nM) in 90% of the healthy population, and <10 µg/ml (100 nM) in 99% of healthy individuals. Plasma CRP concentrations can, e.g., be measured by an immunoassay. Plasma CRP concentrations can, e.g. be measured by homogeneous assay formats or ELISA.

Serum amyloid A (=SAA) is an acute phase protein of low molecular weight of 11.7 kDa. It is predominantly synthesized by the liver in response to IL-1, IL-6 or TNF-stimulation and is involved in the regulation of the T-cell dependent immune response. Upon acute events the concentration of SAA increases up to 1000-fold reaching one milligram per milliliter. It is used to monitor inflammation in diseases as divers as cystic fibrosis, renal graft refection, trauma or infections. In rheumatoid arthritis is has in certain cases been used as a substitute for CRP, but, SAA is not yet as widely accepted.

S100-proteins form a constantly increasing family of $Ca^{2+}$-binding proteins that today includes more than 20 members. The physiologically relevant structure of S100-proteins is a homodimer but some can also form heterodimers with each other, e.g., S100A8 and S100A9. The intracellular functions range from regulation of protein phosphorylation, of enzyme activities, or of the dynamics of the cytoskeleton to involvement in cell proliferation and differentiation. As some S100-proteins are also released from cells, extracellular functions have been described as well, e.g., neuronal survival, astrocyte proliferation, induction of apoptosis and regulation of inflammatory processes. S100A8, S100A9, the heterodimer S100A8/A9 and S100A12 have been found in inflammation with S100A8 responding to chronic inflammation, while S100A9, S100A8/A9 and S100A12 are increased in acute inflammation. S100A8, S100A9, S100A8/A9 and S100A12 have been linked to different diseases with inflammatory components including some cancers, renal allocraft rejection, colitis and most importantly to RA (Burmeister, G., and Gallacchi, G., Inflammopharmacology 3 (1995) 221-230; Foell, D., et al., Rheumathology 42 (2003) 1383-1389).

sE-selectin (soluble endothelial leukocyte adhesion molecule-1, ELAM-1) is a 115 kDa, type-I transmembrane glycoprotein expressed only on endothelial cells and only after activation by inflammatory cytokines (IL-1β, TNF-α) or endotoxin. Cell-surface E-selectin is a mediator of the rolling attachment of leucocytes to the endothelium, an essential step in extravasion of leucocytes at the site of inflammation, thereby playing an important role in localized inflammatory response. Soluble E-selectin is found in the blood of healthy individuals, probably arising from proteolytic cleavage of the surface-expressed molecule. Elevated levels of sE-selectin in serum have been reported in a variety of pathological conditions (Gearing, A. J. and Hemingway, I., Ann. N.Y. Acad. Sci. 667 (1992) 324-331).

In some embodiments a marker for use in a combination with protein ASC in the method according to the present disclosure is selected from the group consisting of CRP, interleukin-6, serum amyloid A and S100. In a further embodiment according to the in vitro method of the present disclosure the value determined for ASC is combined with the determined value of at least one further marker selected from the group consisting of CRP, interleukin-6, serum amyloid A, S100 and E-selectin. In an embodiment the present disclosure relates to the use of the marker combination ASC and C-reactive protein (CRP) in the assessment of COPD. In an embodiment the present disclosure relates to the use of the marker combination ASC and interleukin-6 (IL-6) in the assessment of COPD. In an embodiment the present disclosure relates to the use of the marker combination ASC and serum amyloid A in the assessment of COPD. In an embodiment the present disclosure relates to the use of the marker combination ASC and S100 in the assessment of COPD.

In a further embodiment the present disclosure relates to the use of a marker panel comprising protein ASC and CRP in the in vitro assessment for the presence or absence of COPD in a serum or plasma sample, wherein a concentration of protein ASC above a reference concentration for protein ASC and a concentration of protein CRP above a reference concentration for protein CRP is indicative for the presence of COPD.

In a further embodiment the present disclosure relates to the use of a marker panel comprising protein ASC and CRP in the in vitro assessment for the presence or absence of COPD in a serum or plasma sample, wherein a concentration of protein ASC equal or below to a reference concentration for protein ASC and a concentration of protein CRP above a reference concentration for protein CRP is indicative for the absence of COPD.

Marker panels in one embodiment are combined within a single test device, e.g. on a chip or in an array format. A marker panel according to the present disclosure is in an embodiment determined using a bio-chip array (protein array) technique. An array is a collection of addressable individual markers. Such markers can be spacially addressable, such as arrays contained within microtiter plates or printed on planar surfaces where each marker is present at distinct X and Y coordinates. Alternatively, markers can be addressable based on tags, beads, nanoparticles, or physical properties. A bio-chip array can be prepared according to the methods known to the ordinarily skilled artisan (see for example, U.S. Pat. No. 5,807,522; Robinson, W. H., et al., Nat. Med. 8 (2002) 295-301; Robinson, W. H., et al., Arthritis Rheum. 46 (2002) 885-893). Array as used herein refers to any immunological assay with multiple addressable markers. A bio-chip array, also known to the skilled artisan as microarray, is a miniaturized form of an array.

The terms "chip", "bio-chip", "polymer-chip" or "protein-chip" are used interchangeably and refer to a collection of a large number of probes, markers or biochemical markers arranged on a shared substrate which could be a portion of a silicon wafer, a nylon strip, a plastic strip, or a glass slide.

An "array," "macroarray" or "microarray" is an intentionally created collection of substances, such as molecules, markers, openings, microcoils, detectors and/or sensors, attached to or fabricated on a substrate or solid surface, such as glass, plastic, silicon chip or other material forming an array. The arrays can be used to measure the levels of large numbers, e.g., tens, thousands or millions, of reactions or combinations simultaneously. An array may also contain a small number of substances, e.g., one, a few or a dozen. The substances in the array can be identical or different from each other. The array can assume a variety of formats, e.g., libraries of soluble molecules, libraries of immobilized molecules, libraries of immobilized antibodies, libraries of compounds tethered to resin beads, silica chips, or other solid supports. The array could either be a macroarray or a microarray, depending on the size of the pads on the array. A macroarray generally contains pad sizes of about 300 microns or larger and can be easily imaged by gel and blot scanners. A microarray would generally contain pad sizes of less than 300 microns.

A "solid support" is insoluble, functionalized, polymeric material to which library members or reagents may be attached or covalently bound (often via a linker) to be immobilized or allowing them to be readily separated (by filtration, centrifugation, washing etc.) from excess reagents, soluble reaction by-products, or solvents.

In an embodiment the present disclosure relates to a bio-chip array comprising the marker protein ASC and optionally one or more other marker protein of COPD. The present disclosure also provides in an embodiment a bio-chip array for performing the method according to the present disclosure to specifically determine the concentration of protein ASC and of one or more other marker selected from the group consisting of proteins ARMET, NNMT, FEN1, APEX1 and Seprase, and optionally auxiliary reagents for performing the measurement.

The present disclosure also provides in an embodiment a bio-chip array for performing the method according to the present disclosure to specifically determine the concentration of protein ASC and of one or more other marker selected from the group consisting of proteins ARMET, NNMT, FEN1, APEX1 and Seprase, and optionally auxiliary reagents in the assessment of the presence or absence of COPD.

Kit.

The present disclosure also provides a kit for performing the in vitro method according to the present disclosure comprising the reagents required to specifically determine the concentration of protein ASC.

The present disclosure also provides a kit for performing the method according to the present disclosure comprising the reagents required to specifically determine the concentration of protein ASC and optionally one or more marker protein of COPD as described above, wherein the other markers may be each used individually or in any combination thereof.

The present disclosure also provides a kit for performing the method according to the present disclosure comprising the reagents required to specifically determine the concentration of protein ASC and one or more other marker protein selected from the group consisting of proteins ARMET, NNMT, FEN1, APEX1 and Seprase, and optionally auxiliary reagents for performing the measurement.

In yet a further embodiment the present disclosure relates to a kit comprising the reagents required to specifically determine the concentration of protein ASC and the reagents required to measure the one or more other marker of COPD that are used together in an COPD marker combination. Said kit comprises in an embodiment antibodies or fragments thereof specifically binding to protein ASC. In a further embodiment said antibody fragments in said kit are selected from the group consisting of Fab, Fab', F(ab')2, and Fv. In one embodiment the present disclosure relates to a kit comprising at least two antibodies or fragments thereof specifically binding to at least two non-overlapping epitopes comprised in the ASC sequence of SEQ ID NO:1. In some cases, the at least two antibodies or fragments thereof comprised in a kit according to the present disclosure are monoclonal antibodies. Said kit further comprises in an embodiment a bio-chip on which the antibodies or fragments thereof are immobilized.

In a further embodiment the present disclosure relates to an in vitro diagnostic medical device (IVD) for carrying out the in vitro method for assessing COPD according to the present disclosure. A "diagnostic device" as used herein refers to an in vitro diagnostic medical device (IVD) if it is a reagent, calibrator, control material, kit, specimen receptacle, software, instrument, apparatus, equipment or system, whether used alone or in combination with other diagnostic goods for in vitro use. It, for example, will be generally intended by the manufacturer to be used in vitro for the examination of samples or specimens derived from the human body, solely or principally for the purpose of giving information about a concentration of a marker, physiological or pathological state, a congenital abnormality or to determine safety and compatibility with a potential recipient, or to monitor therapeutic measures.

The following examples, sequence listing, and figures are provided for the purpose of demonstrating various embodiments of the instant disclosure and aiding in an understanding of the present disclosure, the true scope of which is set forth in the appended claims. These examples are not intended to, and should not be understood as, limiting the scope or spirit of the instant disclosure in any way. It should also be understood that modifications can be made in the procedures set forth without departing from the spirit of the disclosure.

ILLUSTRATIVE EMBODIMENTS

The following comprises a list of illustrative embodiments according to the instant disclosure which represent various embodiments of the instant disclosure. These illustrative embodiments are not intended to be exhaustive or limit the disclosure to the precise forms disclosed, but rather, these illustrative embodiments are provided to aide in further describing the instant disclosure so that others skilled in the art may utilize their teachings.

1. An in vitro method for assessing chronic obstructive pulmonary disease (COPD) in a human subject, comprising
a) determining the concentration of protein ASC in a serum, plasma, or whole blood sample, and
b) comparing the concentration of protein ASC determined in step (a) with a reference concentration of protein ASC, wherein a concentration of protein ASC above a reference concentration is indicative for COPD.
2. The method according to embodiment 1, wherein the protein ASC is measured in an immunoassay procedure.
3. The method according to embodiment 2, wherein the immunoassay procedure is an enzyme-linked immunoassay (ELISA).
4. The method according to embodiments 2 and 3, wherein ASC is measured in a sandwich assay format.
5. The method according to embodiments 2 and 3, wherein ASC is measured in a competitive assay format.
6. Use of protein ASC in the in vitro assessment of COPD in a human serum, plasma, or whole blood sample, wherein a concentration of protein ASC above a reference concentration for protein ASC is indicative for COPD.
7. Use of a marker panel comprising protein ASC and one or more other marker for COPD in the in vitro assessment of COPD in a human serum, plasma, or whole blood sample, wherein a concentration of protein ASC above a reference concentration for protein ASC is indicative for COPD.
8. Use of the marker panel according to embodiment 7, wherein the one or more other marker for COPD is selected from the group consisting of proteins ARMET, NNMT, FEN1, APEX1 and Seprase.
9. Use of the marker panel according to embodiment 8 comprising protein ASC and protein NNMT.
10. Use of the marker panel according to embodiment 8 comprising proteins ASC, NNMT and Seprase.
11. Use of the marker panel according to embodiment 8 comprising proteins ASC, NNMT, Seprase and ARMET.
12. Use of a method according to any one of the embodiments 1 to 5 to differentiate COPD from other types of lung diseases, for example asthma.
13. An in vitro diagnostic medical device for carrying out the method according to any one of the embodiments 1 to 5.
14. A kit for performing the method according to any one of embodiments 1 to 5 comprising the reagents required to specifically determine the concentration of protein ASC.

EXAMPLES

Example 1

COPD Study Population

Sources of Serum Samples:
In order to identify COPD-specific proteins as potential diagnostic markers for COPD, serum samples were derived from well-characterized patients with COPD (ATS classification system according table 1) in a national multi-center study. From each sample donor, spirometry was performed. Lung function, other diagnostic tests as well as reason for transferal, diagnosis and comorbidities were documented in a specific Case Report Form (CRF). The COPD samples have been evaluated in comparison with control samples obtained from control groups 1-4 as shown in table 2.
Serum Sample Preparation:
Serum samples were drawn into a serum tube and allowed to clot for at least 60 minutes up to 120 minutes at room temperature. After centrifugation (10 min, 2000 g), the supernatant was divided into 1 ml aliquots and frozen at −70° C. Before measurement, the samples were thawed, re-aliquoted into smaller volumes appropriate for prototype assays and reference assays and refrozen. Samples were thawed immediately before analysis. Therefore, each sample in the panel had only two freeze-thaw cycles before measurement.

Example 2.1

Generation of Antibodies to the Marker Protein ASC

Polyclonal antibody to the marker protein ASC is generated for further use of the antibody in the measurement of serum and plasma and blood levels of ASC by immunodetection assays, e.g. Western Blotting and ELISA
Recombinant Protein Expression in E. coli:
In order to generate antibodies against ASC, the recombinant antigen is produced in E. coli: Therefore, the ASC coding region is PCR amplified from the full-length cDNA clone IRAT p970H075D obtained from the German Resource Center for Genome Research (RZPD, Berlin, Germany) using suitable forward and reverse primers.
The forward primer features (besides the EcoRI cloning and ribosomal binding sites) oligonucleotides coding for an N-terminal MRGSHHHHHHIEGR peptide extension (SEQ ID NO: 8) introduced in-frame to the ASC polypeptide. The EcoRI/BamHI digested PCR fragment is ligated into the corresponding pQE-30 (Qiagen, Hilden, Germany) vector fragment which is subsequently transformed into E. coli XL1-blue competent cells. After sequence analysis, the plasmid is transformed into E. coli BL21 competent cells for expression under the IPTG-inducible T5 promoter of the pQE vector series following the manufacturer's instructions.
For purification of the MRGSHHHHHHIEGR-ASC fusion protein, 1l of an over-night induced bacterial culture is pelleted by centrifugation and the cell pellet is resuspended in 20 mM sodium-phosphate buffer, 500 mM sodium chloride, pH 7.4 containing 1 mg/ml lysozyme and Complete™ EDTA-free protease inhibitor tablets. The cells are disrupted by ultrasonication and insoluble material is pelleted by centrifugation and the supernatant is applied to Ni-nitrilotriacetic acid (Ni-NTA) metal-affinity chromatography: The column is washed with several bed volumes of lysis buffer followed by washes with 20 mM sodium-phosphate buffer, 500 mM sodium chloride, 20 mM imidazol, pH 7.4. Finally, bound antigen is eluted with an imidazol gradient from 20 to 500 mM in 20 mM sodium-phosphate buffer, 500 mM sodium chloride, pH 7.4 and stored in 75 mM HEPES-buffer, pH 7.5, 100 mM sodium chloride, 1 mM EDTA, 6.5% sucrose at 4° C.

Generation of Polyclonal Antibodies:

a) Immunization:

For immunization, a fresh emulsion of the protein solution (100 µl/ml protein ASC) and complete Freund's adjuvant at the ratio of 1:1 is prepared. Each rabbit is immunized with 1 ml of the emulsion at days 1, 7, 14 and 30, 60 and 90. Blood is drawn and resulting anti-ASC serum is used as described hereinbelow.

b) Purification of IgG (Immunoglobulin G) from Rabbit Serum by Sequential Precipitation with Caprylic Acid and Ammonium Sulphate:

One volume of rabbit serum is diluted with 4 volumes of acetate buffer (60 mM, pH 4.0). The pH is adjusted to 4.5 with 2 M Tris-base. Caprylic acid (25 µl/ml of diluted sample) is added drop-wise under vigorous stirring. After 30 min the sample is centrifuged (13000×g, 30 min, 4° C.), the pellet discarded and the supernatant collected. The pH of the supernatant is adjusted to 7.5 by the addition of 2 M Tris-base.

The immunoglobulin in the supernatant is precipitated under vigorous stirring by the drop-wise addition of a 4 M ammonium sulfate solution to a final concentration of 2M. The precipitated immunoglobulins are collected by centrifugation (8000×g, 15 min, 4° C.).

The supernatant is discarded. The pellet is dissolved in 10 mM NaH$_2$PO$_4$/NaOH, pH 7.5, 30 mM NaCl and exhaustively dialyzed. The dialysate is centrifuged (13000×g, 15 min, 4° C.) and filtered (0.2 µm).

c) Biotinylation of Polyclonal Rabbit IgG:

Polyclonal rabbit IgG is brought to 10 mg/ml in 10 mM NaH$_2$PO$_4$/NaOH, pH 7.5, 30 mM NaCl. Per ml IgG solution 50 µl Biotin-N-hydroxysuccinimide (3.6 mg/ml in DMSO) are added. After 30 min at room temperature, the sample is chromatographed on Superdex 200 (10 mM NaH$_2$PO$_4$/NaOH, pH 7.5, 30 mM NaCl). The fractions containing biotinylated IgG are collected.

d) Immunosorption of Polyclonal Rabbit IgG:

For the ASC immunosorber 10 mg purified recombinant ASC is coupled to 1 ml CNBr-activated Sepharose™ 4B (GE Healthcare, Germany Catalog No. 17-04-30-01) according to the manufacturer's protocol. This affinity column is loaded with 100 mg polyclonal rabbit IgG in PBS, 0.05% Tween 20 followed by washes with a) PBS, b) 0.5 M sodium chloride, 0.05% Tween 20, c) 30 mM sodium chloride. The bound fraction is eluted with 0.5 M glycine, 150 mM sodium chloride adjusted to pH 2.1 with hydrochloric acid and immediately brought to a neutral pH by the addition of 1 M Tris-base. The eluate is concentrated to 10 mg/ml and chromatographed on a TSK-Gel G3000SW gelfiltration column (Sigma-Aldrich, Germany, catalogue No. 815103) in PBS. The fractions containing IgG monomers are collected.

Example 2.2

CRP

The marker protein CRP is measured using a homogenous assay (Hitachi) distributed by Roche Diagnostics, Mannheim (FRG).

Example 3

ELISA for the Measurement of ASC in Human Serum or Plasma Samples

For detection of ASC in human serum or plasma samples, a sandwich ELISA was developed. For capture and detection of the antigen, aliquots of the antibody against ASC were conjugated with biotin and digoxygenin, respectively.

Samples (20 µl) were mixed in separate wells of a streptavidin-coated microtiter plate with 100 µl of antibody reagent containing 0.12 µg/ml of each, biotin labeled and digoxigenin labeled antibodies in incubation buffer (40 mM phosphate, 200 mM sodium tartrate, 10 mM EDTA, 0.05% phenol, 0.1% polyethylene glycol 40000, 0.1% Tween 20, 0.2% BSA, 0.1% bovine IgG, 0.02% 5-Bromo-5-Nitro-1,3-Dioxane adjusted to pH 7.4, supplemented with 200 µg/ml polymeric monoclonal mouse IgG Fab-fragments for elimination of human anti-rat antibody response (HARA); Roche Diagnostics GmbH, Mannheim, Germany, Catalog #11096478-001).

After incubation for one hour plates were washed three times with washing buffer (10 mM Tris, 150 mM NaCl, 0.05% Tween 20).

In a next step, wells were incubated with 30 mU/ml anti-digoxigenin-HRP conjugate (Roche Diagnostics GmbH, Mannheim, Germany, Catalog #1633716) in Universal Conjugate Buffer (Roche Diagnostics GmbH, Mannheim, Germany, Catalog #11684825) for 60 min and washed as before.

Wells were then incubated for 30 min. with 100 µl of TMB substrate solution (Roche Diagnostics GmbH, Mannheim, Germany, Catalog #12034425). Adding of 2N sulfuric acid (50 µl) stopped the color development and switched the blue color into yellow. OD was measured at 450 nm with an ELISA reader.

All incubations were at room temperature. Samples of human serum or plasma were pre-diluted with incubation buffer ad 5%. For calibration, a human serum was used as a standard. It was diluted with incubation buffer ad 2/4/8/16/32% to make calibrators with arbitrarily given values of 2/4/8/16/32 Units/ml, respectively.

The equation of the calibration curve was calculated by non-linear least-squares curve-fitting (Wiemer-Rodbard) and used for converting the absorbance reading of a well into the corresponding concentration value. The result was multiplied by the pre-dilution factor to get the concentration of the respective sample itself.

Example 4

ASC as a Serum Marker for COPD

Serum samples derived from 123 well-characterized COPD patients of the ATS COPD stage 0-IV classification shown in table 1 are used. The study population is shown in Table 2.

TABLE 2

Study population

| Sample type | Number of samples |
| --- | --- |
| COPD Stage 0-IV (according to ATS classification shown in table 1) | 123 |
| Control 1: healthy nonsmokers (normal lung function) | 50 |
| Control 2: healthy smokers & former smokers (normal lung function) | 88 |
| Control 3: healthy individuals with occupational risk (asbestos, silica, dust, . . . ) | 48 |
| Control 4: asthma patients | 26 |

Figure 2:
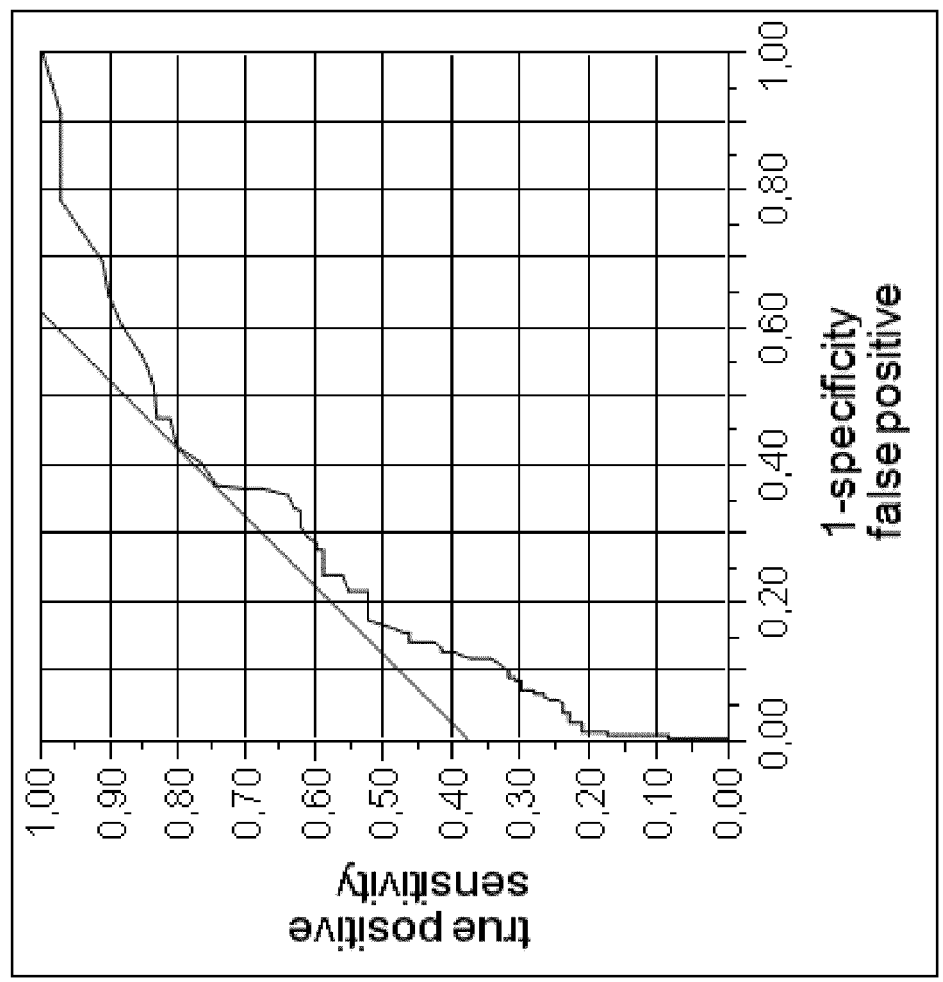
FIG. 2 shows the plot of the receiver operator characteristics (ROC-plot) of CRP in COPD samples with an AUC of 0.74 (ROC 74%) for the assessment of 123 samples obtained from patients with COPD as compared to 186 control samples obtained from healthy control patients (X-axis: 1-specificity (false positive); Y-axis: sensitivity (true positive)).

The serum concentration of protein ASC in the COPD samples is evaluated in comparison to control samples (Control 1, 2 and 3) obtained from obviously healthy individuals (=control cohort), and asthma patients (Control 4), with an AUC of 0.88 (Table 3). A receiver operator characteristic curve (ROC) of the results represented in Table 3 of marker ASC is shown in FIG. 1. Data determined for the inflammation marker CRP are shown in FIG. 2. The AUC of marker ASC is higher than the AUC of CRP.

TABLE 3

ROC analysis of the marker protein in comparison to CRP

| Marker | ASC | CRP |
|---|---|---|
| ROC | 88% | 74% |

The cut-off value was determined in the control collective by calculation of the 95% quantile resulting in a 95% specificity. The diagnostic potential of the biomarker was evaluated either by calculating the receiver operator characteristic curves (ROC) (Table 3) or the clinical sensitivity at the preset specificity of 95% (Table 4). The sensitivity for a cut-off vs healthy individuals (Control 1) for COPD of marker ASC is 76%. With a cut-off value that yields 95% specificity on the respective control cohort (Control 1, 2 and 3: namely healthy nonsmokers, smokers, former smokers and individuals with occupational risk to develop COPD), the sensitivity of marker ASC for a cut-off for general screening for COPD is 60%.

TABLE 4

Sensitivity and specificity of the marker protein in comparison to CRP

| Marker | ASC | CRP |
|---|---|---|
| specificity | 95% | 95% |
| sensitivity (cut-off control 1) | 76% | 31% |
| sensitivity (cut-off control 1, 2 and 3) | 60% | 24% |

When applying a cut-off (95% specificity) based on control 1 (healthy control according to table 2) or based on control 1, 2 and 3 (screening controls according to table 2), the sensitivity of marker ASC is higher than the sensitivity of CRP (Table 4). This is also reflected by ROC analysis, wherein marker ASC exhibit a greater AUC than the marker CRP (Table 3).

The marker ASC has a slightly improved accuracy in the classification of COPD patients into ATS stages 0-IV as compared to CRP.

Example 5

ASC as a Serum Marker to Differentiate Human COPD Vs Asthma

Samples derived from 123 well-characterized COPD patients according to ATS COPD stage 0-IV classification shown in table 1 as well as samples derived from 26 asthma patients (Control 4 as shown in Table 2) were analysed using the marker ASC. With a cut-off value that yields 95% specificity vs the asthma control cohort, the sensitivity for COPD is 55% (Table 5).

The sensitivity to differentiate COPD from asthma of marker ASC is higher than the sensitivity of the inflammation marker CRP.

TABLE 5

Differentiation of COPD vs asthma by usage of marker protein

| Marker | ASC | CRP |
|---|---|---|
| specificity (vs. asthma) | 95% | 95% |
| sensitivity (for COPD) | 55% | 25% |
| ROC | 87% | 70% |

Figure 5:
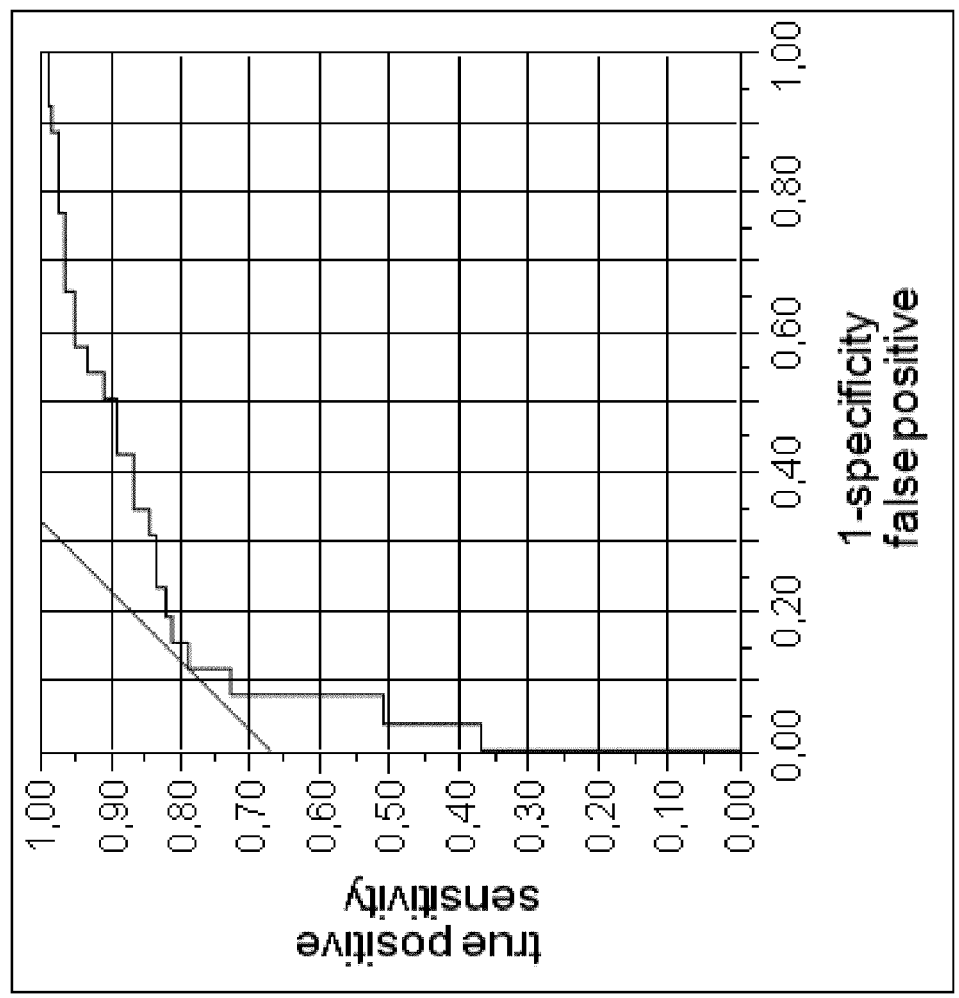
FIG. 5 shows the plot of the receiver operator characteristics (ROC-plot) of protein ASC in COPD samples with an AUC of 0.87 (ROC 87%) for the assessment of 123 samples obtained from patients with COPD as compared to 26 control samples obtained from patients with asthma (X-axis: 1-specificity (false positive); Y-axis: sensitivity (true positive)).
Figure 6:
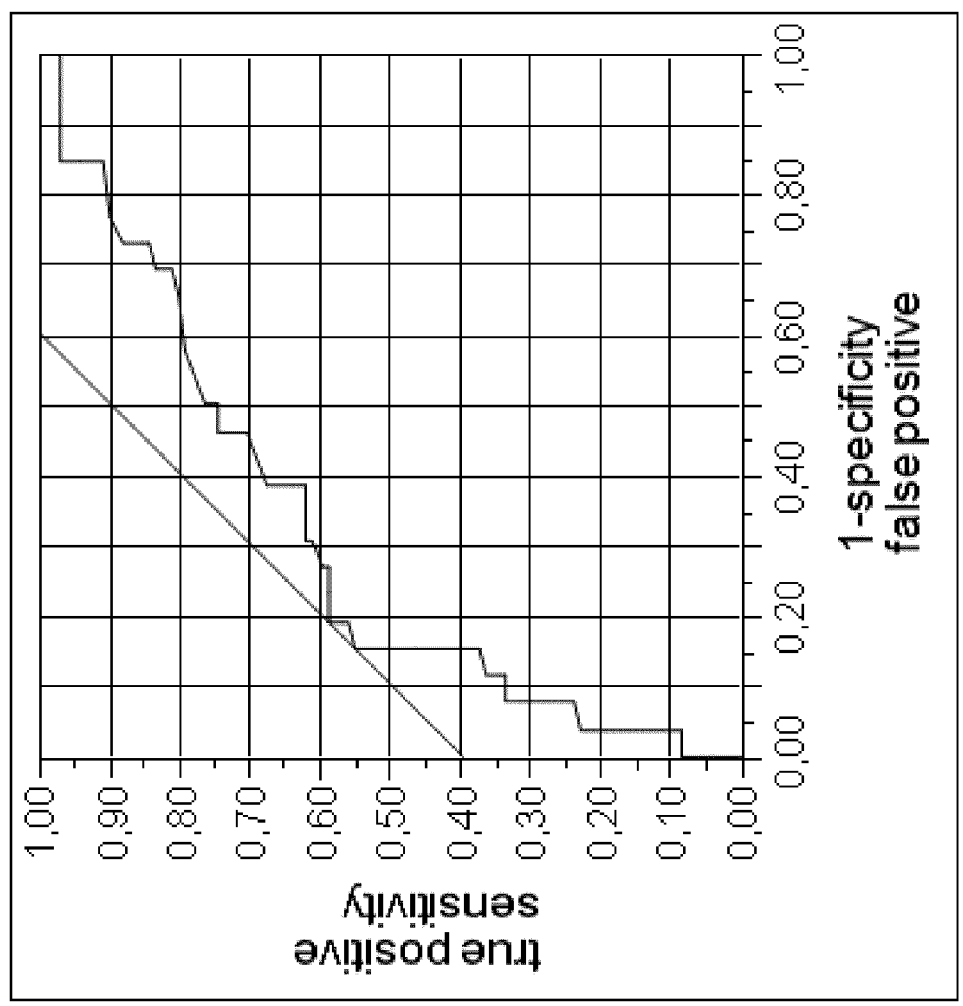
FIG. 6 shows the plot of the receiver operator characteristics (ROC-plot) of CRP in COPD samples with an AUC of 0.70 (ROC 70%) for the assessment of 123 samples obtained from patients with COPD as compared to 26 control samples obtained from patients with asthma (X-axis: 1-specificity (false positive); Y-axis: sensitivity (true positive)).

A graphical representation of the results of marker ASC is shown in FIG. 5 as a receiver operator characteristic curves (ROC). The results for the inflammation marker CRP is shown in FIG. 6 as a receiver operator characteristic curves (ROC).

Figure 7:
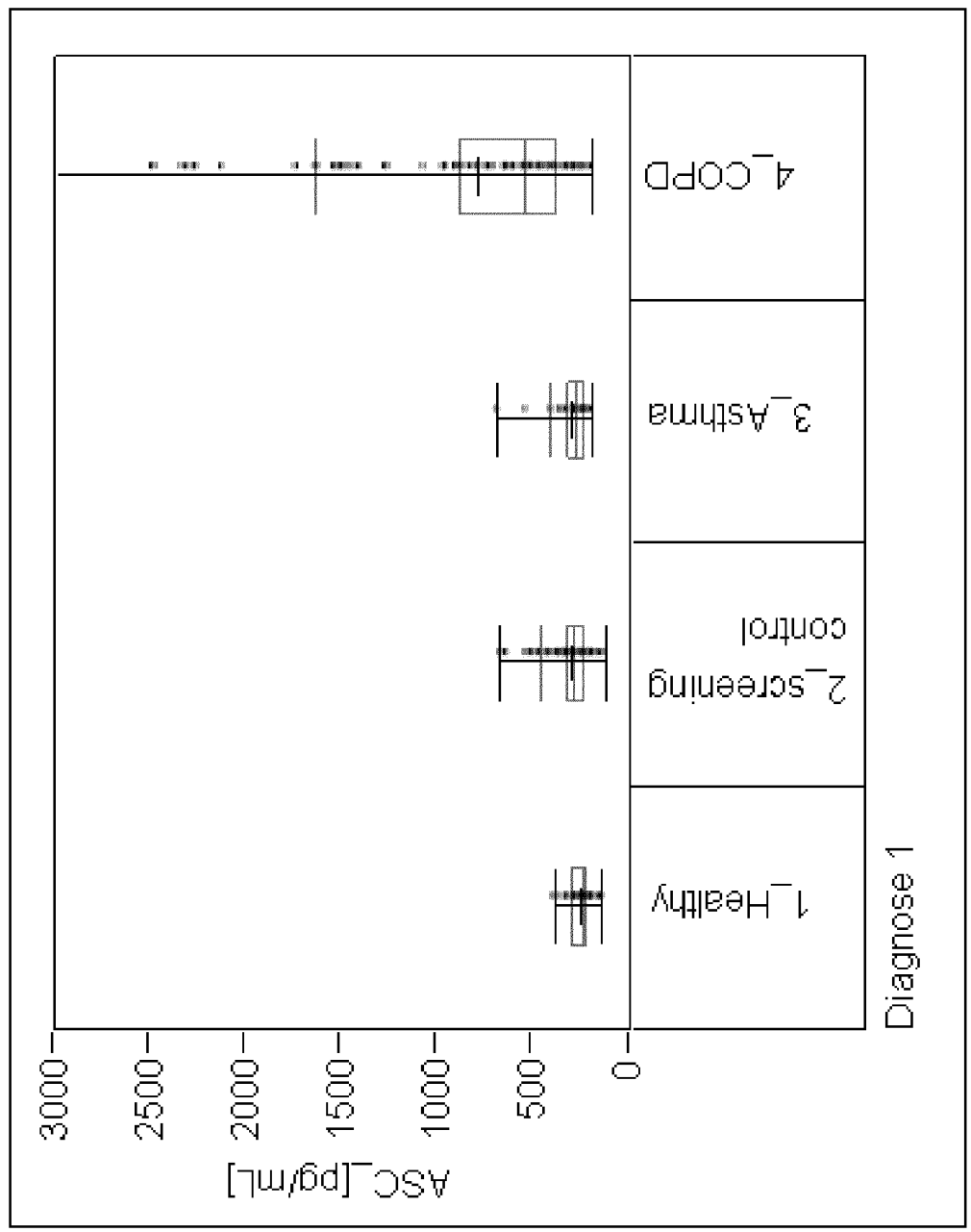
FIG. 7 shows a box plot distribution of the determined ASC serum concentration [pg/ml] according to 123 COPD samples of stadium 0-IV (4_COPD), 50 healthy (1_Healthy), 135 screening controls (2_screening control) and 26 asthma patient samples (3_Asthma) (the y-axis is adjusted for better 'visualization').

The data determined for protein ASC in COPD samples have been used to calculate the box-plot shown in FIG. 7 based on the data shown in Table 6, representing the correlation of the serum concentration of protein ASC with the ATS COPD stages 0-IV (n=123, as shown in Table 2) vs samples from healthy subjects (n=50), samples from screening control (n=135) and asthma patients (n=26). While mean values of controls (healthy, screening control and asthma) range between 273 and 312 pg/ml, ASC concentrations of COPD patients are significantly higher with a mean value of 807 pg/ml. Results are represented in Table 6.

TABLE 6

Variability of ASC

| ASC | N | minimum [pg/mL] | maximum [pg/mL] | mean value [pg/mL] | std. div. | std. error mean value | 95% KI lower | 95% KI upper |
|---|---|---|---|---|---|---|---|---|
| 1_Healthy | 50 | 157.841 | 407.744 | 272.513 | 61.66398 | 8.720604 | 254.9883 | 290.0377 |
| 2_Screening control | 135 | 139.248 | 680.662 | 311.7089 | 92.8116 | 7.987951 | 295.9101 | 327.5077 |
| 3_Asthma | 26 | 205.327 | 706.382 | 312.3982 | 109.8092 | 21.53536 | 268.0453 | 356.7511 |
| 4_COPD | 123 | 203.242 | 7664 | 807.4792 | 821.0494 | 74.03153 | 660.9264 | 954.0321 |

Figure 3:
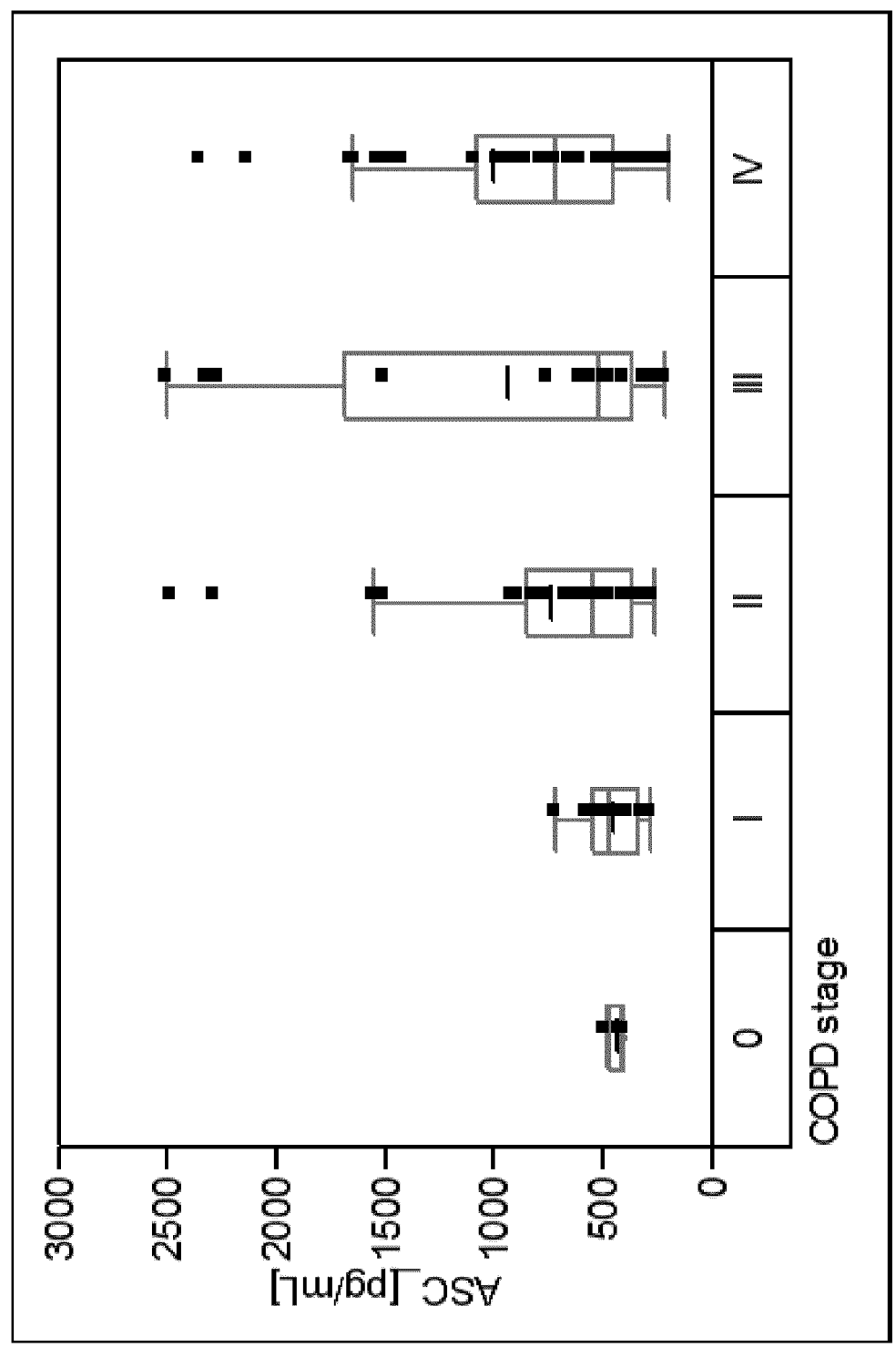
FIG. 3 shows the box blot distribution of the determined ASC serum concentration values according to the COPD stages 0-IV of the 123 COPD samples (COPD stadium as described in Table 1).
Figure 4:
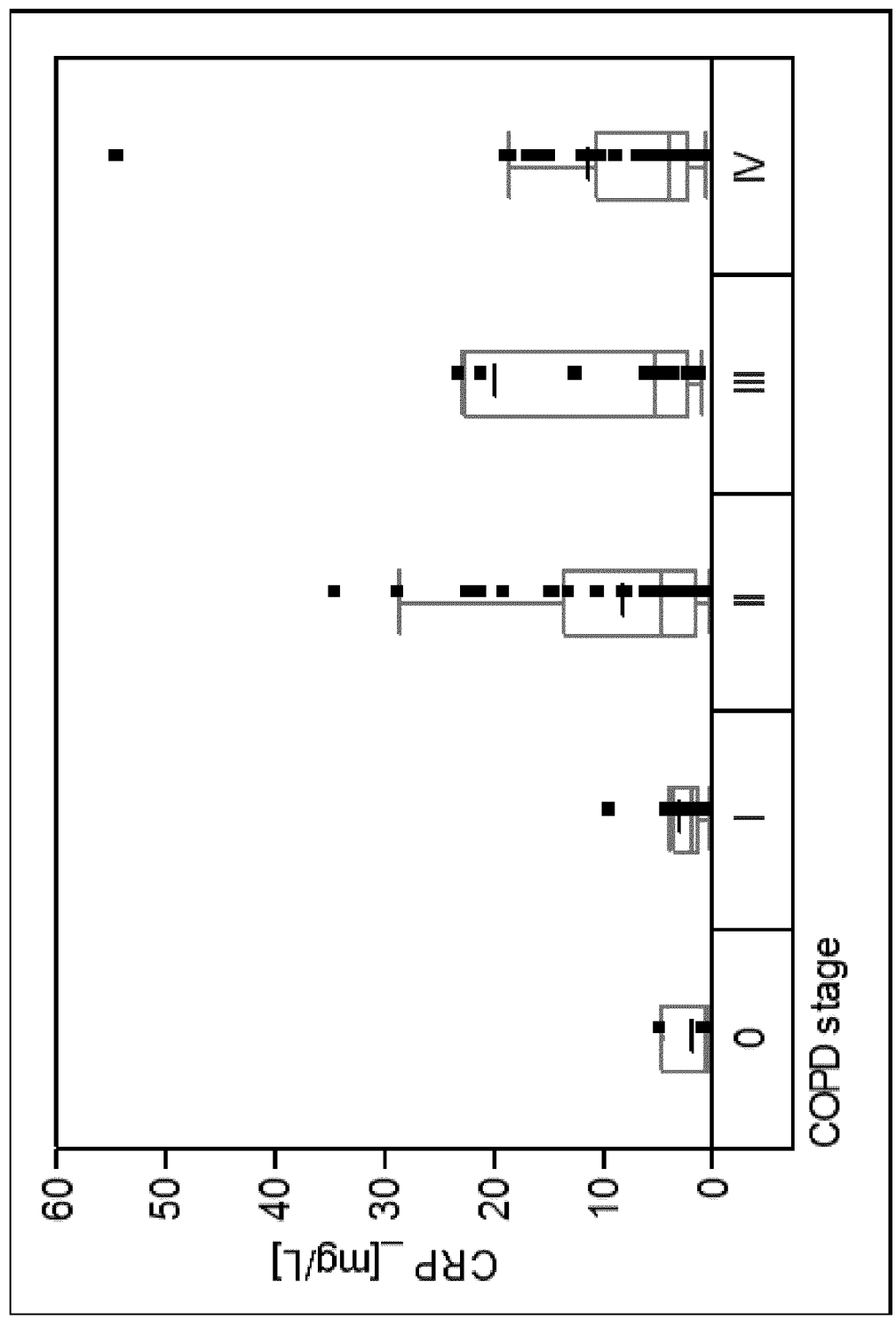
FIG. 4 shows the box plot distribution of the determined CRP serum concentration according to the COPD stages 0-IV of the 123 COPD samples (COPD stadium as shown in Table 1).

The data determined for protein ASC in COPD samples according ATS COPD stages 0-IV have been used to calculate the box-plot shown in FIG. 3, representing the correlation of the serum concentration of protein ASC with the ATS COPD stages 0-IV. The data determined for the inflammation marker CRP within each sample classified according to the ATS COPD stages 0-IV have been used to calculate the box-plot shown in FIG. 4, representing the correlation of the serum concentration of CRP with the COPD stadium.

Example 6

Marker Combinations/Statistical Analysis and Results

Penalized Logistic Regression (PLR) was used as a mathematical model for marker combinations as implemented in the R-toolbox "glmnet" (http://cran.r-project.org/). To search for an additional marker, the initial marker entered in an unpenalized way the model, whereas all other markers were subject to penalization.

The algorithm optimisation (namely the selection of the penalization type and its penalization parameter) was carried out by an internal repeated 10-fold cross-validation, whereas the derivation of the performance parameters (sensitivity and specificity) was based on an outer repeated 10-fold cross-validation.

The original dataset was split into 10 parts, afterwards 9 of these parts formed the training-set and the 10th part the test set. The training set was then also split into 10 parts, were 9 of these parts formed the sub-training set and the 10th part the sub-testset. With these sub-datasets the penalization parameter was optimized based on the number of additional markers. With this optimized value the PLR was applied on the whole training set to generate a diagnostic rule. A threshold on the estimated posterior case-probabilities was determined on the controls as well as on the cases of the training set to achieve an apparent specificity and sensitivity of 90% for the multivariate diagnostic rule. This rule was then applied to the test set to estimate sensitivity and specificity at the given threshold. The external 10-fold cross-validation was repeated 50 times, the internal cross-validation 25 times.

A close analysis of the individual runs from cross validation revealed that the best additional marker for ASC is NNMT, as it was selected as best additional marker in all runs. The best model with two additional markers is ASC plus NNMT and Seprase. The best model with three additional markers is ASC plus NNMT, Seprase and ARMET.

Samples derived from 123 well-characterized COPD patients according to ATS COPD stage 0-IV classification, as shown in table 2, as well as a control cohort consisting of 161 samples derived from healthy (n=136) and asthma patients (n=25) were analysed.

In Table 7 the classification performance for these combinations on training and testset are given, based on a specificity of 90%.

The results in Table 7 clearly show, that by combination of one additional marker the sensitivity can be significantly improved compared to ASC as single marker without any loss of specificity.

TABLE 7

| Marker combinations on a specificity of 90% | | | | |
|---|---|---|---|---|
| Combination | Train. Sens. [log] | Train Spec. [log] | Test. Sens. [log] | Test Spec. [log] |
| ASC + NNMT | 0.77 (0.75-0.8) | 0.9 (0.89-0.9) | 0.77 (0.76-0.78) | 0.89 (0.88-0.91) |

TABLE 7-continued

| Marker combinations on a specificity of 90% | | | | |
|---|---|---|---|---|
| Combination | Train. Sens. [log] | Train Spec. [log] | Test. Sens. [log] | Test Spec. [log] |
| ASC + NNMT + Seprase | 0.83 (0.77-0.87) | 0.9 (0.89-0.9) | 0.82 (0.8-0.85) | 0.89 (0.88-0.91) |
| ASC + NNMT + Seprase + ARMET | 0.83 (0.77-0.87) | 0.9 (0.89-0.9) | 0.82 (0.8-0.84) | 0.89 (0.88-0.9) |

In Table 8 the classification performance for these combinations on training and testset are given, based on a sensitivity of 90%. The results in Table 8 clearly show, that by combination of one additional marker the specificity can be significantly improved compared to ASC as single marker without any loss of sensitivity.

TABLE 8

| Marker combinations on a sensitivity of 90% | | | | |
|---|---|---|---|---|
| Combination | Train. Sens. [log] | Train Spec. [log] | Test. Sens. [log] | Test Spec. [log] |
| ASC + NNMT | 0.9 (0.89-0.9) | 0.72 (0.69-0.76) | 0.89 (0.87-0.9) | 0.72 (0.7-0.74) |
| ASC + NNMT + Seprase | 0.9 (0.89-0.9) | 0.74 (0.71-0.83) | 0.89 (0.88-0.9) | 0.75 (0.74-0.76) |
| ASC + NNMT + Seprase + ARMET | 0.9 (0.89-0.9) | 0.74 (0.71-0.83) | 0.89 (0.88-0.9) | 0.75 (0.73-0.77) |

Figure 8:
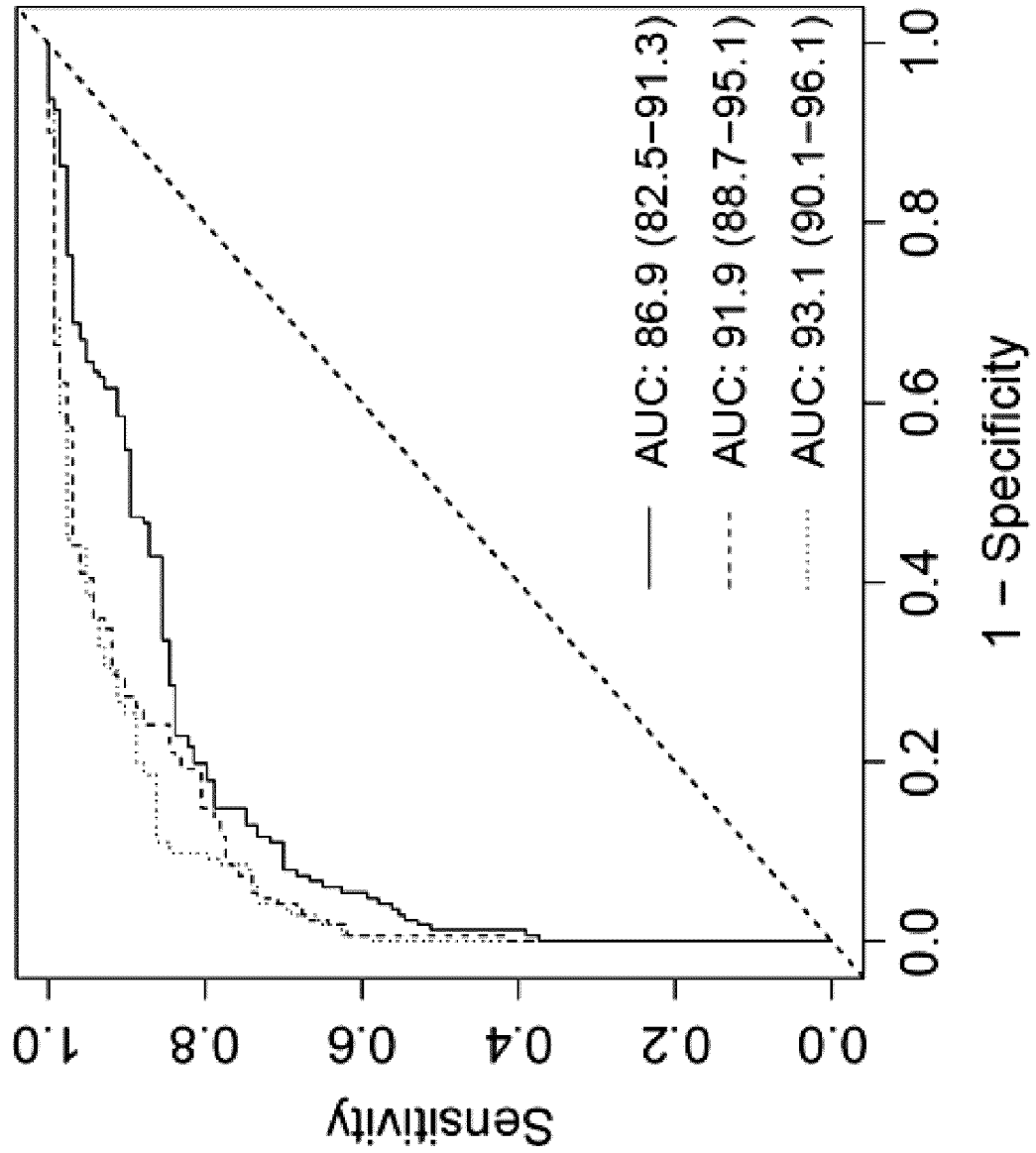
FIG. 8 shows the plot of the receiver operator characteristics (ROC-plot) of protein ASC in COPD samples for ASC (solid line), ASC+NNMT (dashed line) and ASC+NNMT+Seprase (dotted line) marker combinations for the assessment of 123 samples obtained from patients with COPD as compared to 161 control samples obtained from healthy control and asthma patients (X-axis: 1-specificity (false positive); Y-axis: sensitivity (true positive)).

With a cut-off value that yields 90% specificity vs control cohort, the sensitivity for a cut-off for general screening with ASC is 86.9%, with ASC+NNMT is 91.9%, with ASC+NNMT+Seprase is 93.1% and with ASC+NNMT+Seprase+ARMET is 93.1% (4 marker combination not shown in FIG. 8). A graphical representation of the results of marker ASC and marker combinations for up to 3 markers is shown in FIG. 8 as a receiver operator characteristic curves (ROC).

All references cited in this specification are herewith incorporated by reference with respect to their entire disclosure content and the disclosure content specifically mentioned in this specification.

While this disclosure has been described as having an exemplary design, the present disclosure may be further modified within the spirit and scope of this disclosure. This application is therefore intended to cover any variations, uses, or adaptations of the disclosure using its general principles. Further, this application is intended to cover such departures from the present disclosure as come within the known or customary practice in the art to which this disclosure pertains.

What is claimed is:

1. An in vitro method for diagnosing chronic obstructive pulmonary disease (COPD) in a patient, comprising:
    determining a concentration of protein apoptosis-associated speck-like protein containing a caspase-associated recruitment domain (ASC) in a serum, plasma, or whole blood sample obtained from the patient, wherein said step of determining comprises:
    contacting a portion of the sample obtained from the patient with an antibody that specifically binds to protein ASC, thereby forming a complex between the antibody and protein ASC, the antibody having a detectable label;
    separating the complex formed in said step of contacting from antibody not comprising the complex;
    quantifying a signal from the detectable label of the antibody comprising the complex formed in said step of contacting, the signal being proportional to an amount of protein ASC in the sample obtained from the patient, whereby an amount of protein ASC in the sample obtained from the patient is calculated;
    comparing the concentration of protein ASC in the sample determined in said step of determining with a protein ASC reference concentration of about 312 pg/ml;
    providing a diagnosis of COPD in the patient if the concentration of protein ASC in the sample determined in said step of determining is greater than the protein ASC reference concentration.

2. The method according to claim 1, wherein said step of determining comprises an immunoassay procedure.

3. The method according to claim 2, wherein the immunoassay procedure comprises an enzyme-linked immunoassay (ELISA).

4. The method according to claim 2, wherein the immunoassay procedure comprises a sandwich assay format.

5. The method according to claim 2, wherein the immunoassay procedure comprises a competitive assay format.

6. The method according to claim 1, wherein the protein ASC reference concentration has a specificity of 95%.

7. The method of claim 1 further comprising the step of contacting the portion of the sample from the patient with a capture antibody, the capture antibody having specific binding affinity for an epitope of protein ASC not bound by the antibody, thereby forming a complex between the capture antibody and protein ASC, the capture antibody coupled to one of streptavidin and biotin, said step of contacting the portion of the sample with the capture antibody occurring prior to said steps of separating and quantifying, wherein upon said steps of contacting the portion of the sample with the antibody and contacting the portion of the sample with the capture antibody, a complex between the antibody, protein ASC and the capture antibody is thereby formed.

8. The method of claim 1, wherein said step of quantifying a signal comprises use of a computing device.

9. The method of claim 1, wherein said step of contacting and said step of separating comprise use of a medical device.

10. The method of claim 1, further comprising the steps of:
   determining a concentration of protein nicotinamide N-methyltransferase (NNMT) in the serum, plasma, or whole blood sample obtained from the patient; and
   comparing the concentration of protein NNMT in the sample determined in said step of determining with a protein NNMT reference concentration,
   wherein said step of providing a diagnosis comprises providing a diagnosis of COPD in the patient if both the concentration of protein ASC in the sample is greater than the protein ASC reference concentration and the concentration of protein NNMT in the sample is greater than the protein NNMT reference concentration.

11. The method of claim 10, wherein both of the protein ASC reference concentration and the protein NNMT reference concentration have a specificity of 90%.

12. An in vitro method for differentiating between asthma and chronic obstructive pulmonary disease (COPD) in a patient suspected of having asthma, comprising:
   determining a concentration of protein apoptosis-associated speck-like protein containing a caspase-associated recruitment domain (ASC) in a serum, plasma, or whole blood sample obtained from the patient;
   comparing the concentration of protein ASC in the sample determined in said step of determining with a protein ASC reference concentration from a patient having asthma;
   providing a diagnosis of COPD if the concentration of protein ASC in the sample determined in said step of determining is greater than the protein ASC reference concentration.

13. The method of claim 12, wherein the protein ASC reference concentration has a specificity of 95%.

14. The method of claim 12, wherein said step of determining further comprises the steps of:
   contacting a portion of the sample obtained from the patient with an antibody having specific binding affinity for protein ASC, thereby forming a complex between the antibody and protein ASC, the antibody having a detectable label;
   separating the complex formed in said step of contacting from antibody not comprising the complex; and
   quantifying a signal from the detectable label of the antibody comprising the complex formed in said step of contacting, the signal being proportional to an amount of protein ASC in the sample obtained from the patient, whereby an amount of protein ASC in the sample obtained from the patient is calculated.

15. The method of claim 12, further comprising the steps of:
   determining a concentration of protein NNMT in the serum, plasma, or whole blood sample obtained from the patient; and
   comparing the concentration of protein NNMT in the sample determined in said step of determining with a protein NNMT reference concentration,
   wherein said step of providing a diagnosis comprises providing a diagnosis of COPD in the patient if both the concentration of protein ASC in the sample is greater than the protein ASC reference concentration and the concentration of protein NNMT in the sample is greater than the protein NNMT reference concentration.

16. The method of claim 15, wherein both of the protein ASC reference concentration and the protein NNMT reference concentration have a specificity of 90%.

* * * * *